(12) United States Patent
Tseng

(10) Patent No.: US 9,129,741 B2
(45) Date of Patent: Sep. 8, 2015

(54) METHOD AND APPARATUS FOR WIRELESS POWER TRANSMISSION

(75) Inventor: Ryan Tseng, Longwood, FL (US)

(73) Assignee: Qualcomm Incorporated, San Diego, CA (US)

( * ) Notice: Subject to any disclaimer, the term of this patent is extended or adjusted under 35 U.S.C. 154(b) by 1305 days.

(21) Appl. No.: 11/901,158

(22) Filed: Sep. 14, 2007

(65) Prior Publication Data
US 2008/0067874 A1     Mar. 20, 2008

Related U.S. Application Data

(60) Provisional application No. 60/844,478, filed on Sep. 14, 2006.

(51) Int. Cl.
*H01F 5/00* (2006.01)
*H01F 27/28* (2006.01)
*H01F 38/14* (2006.01)
*A61C 17/22* (2006.01)
(Continued)

(52) U.S. Cl.
CPC ............. *H01F 38/14* (2013.01); *A61C 17/224* (2013.01); *H02J 7/025* (2013.01); *H01F 17/0006* (2013.01)

(58) Field of Classification Search
CPC .................................. H01F 5/00; H01F 27/28
USPC ................................................... 336/200, 232
See application file for complete search history.

(56) References Cited

U.S. PATENT DOCUMENTS 3,390,337 A * 6/1968 Beitman, Jr. ............... 455/123
6,249,039 B1 * 6/2001 Harvey et al. .............. 257/531
6,436,299 B1 8/2002 Baarman et al.
(Continued)

FOREIGN PATENT DOCUMENTS

JP    2001085230 A *  3/2001
JP    2003257740 A *  9/2003

OTHER PUBLICATIONS

HotSpotzz Network, "WiFi Market Information and Statistics," Feb. 2003. Online: http://www.hotspotzz.com/resource/WiFi_stats.pdf.
(Continued)

*Primary Examiner* — Tsz Chan
(74) *Attorney, Agent, or Firm* — Knobbe, Martens, Olson & Bear, LLP

(57) ABSTRACT

Embodiments of the invention relate to a method and system for transferring power wirelessly to electronic devices. The system can utilize magnetic coupling between two coils at close proximity to transfer sufficient power to charge an electronic device. Embodiments of the invention pertain to an array of spiral coils that can be used to transmit power for transfer to receiver coils. Potential applications of this technology include charging consumer electronic devices (cell phones, laptops, PDAs, etc), developing hermetically sealed devices for extreme environments, and less invasive transcutaneous energy transfer (TET) systems. Various embodiments of the subject system can be referred to as PowerPad system. Embodiments can incorporate one or more of the following: planar inductors, PCB transformers, and very high frequency power supplies. Embodiments of the invention also pertain to planar inductors having characteristics that allow the production of even magnetic field, as well as systems that incorporate such planar inductors.

24 Claims, 21 Drawing Sheets
(17 of 21 Drawing Sheet(s) Filed in Color)

(51) Int. Cl.
*H02J 7/02* (2006.01)
*H01F 17/00* (2006.01)

(56) References Cited

U.S. PATENT DOCUMENTS

| | | | |
|---|---|---|---|
| 6,529,127 B2* | 3/2003 | Townsend et al. | 340/505 |
| 6,608,291 B1* | 8/2003 | Collins et al. | 219/662 |
| 6,673,250 B2 | 1/2004 | Kuennen et al. | |
| 6,906,495 B2 | 6/2005 | Cheng et al. | |
| 7,042,196 B2 | 5/2006 | Ka-Lai et al. | |
| 7,212,414 B2 | 5/2007 | Baarman | |
| 7,239,110 B2 | 7/2007 | Cheng et al. | |
| 7,248,017 B2 | 7/2007 | Cheng et al. | |
| 2003/0098496 A1* | 5/2003 | Sugiyama et al. | 257/531 |
| 2003/0137370 A1* | 7/2003 | Ishikawa et al. | 333/219 |
| 2003/0186674 A1* | 10/2003 | Keeney et al. | 455/347 |
| 2005/0046538 A1* | 3/2005 | Maruyama | 336/232 |
| 2005/0116683 A1 | 6/2005 | Cheng et al. | |
| 2005/0189910 A1* | 9/2005 | Hui | 320/108 |
| 2005/0275497 A1* | 12/2005 | Ramadan et al. | 336/200 |
| 2006/0043927 A1 | 3/2006 | Beart et al. | |
| 2006/0061323 A1 | 3/2006 | Cheng et al. | |
| 2006/0205381 A1 | 9/2006 | Beart et al. | |
| 2007/0171681 A1 | 7/2007 | Baarman | |

OTHER PUBLICATIONS

WiFi Net News, "Laptop Sales Pass Desktop Sales," Feb. 2006. Online: http://wifinetnews.com/archives/006258.html.
Network World, "Juniper, Foundry size up Router Race," Jun. 2000. Online: http://www.networkworld.com/archive/2000/98086_06-05-2000.html.
CBS News, "Microsoft Debuts Wireless Mouse," Sep. 2003. Online: http://www.cbsnews.com/stories/2003/09/22/tech/main574453.shtml.
Bluetooth, "Bluetooth History," Feb. 2006. Online: http://www.bluetooth.com/Bluetooth/SIG/Who/History/.
Bluetooth Technology, "History of Bluetooth," Jul. 2005. Online: http://www.du.edu/~ccfergus/bluetoothweb/history.htm.
Farber, D., "Highlight Reel from the D conference," ZDNet, Jun. 2006. Online: http://blogs.zdnet.com/BTL/?p=3132.
Splashpower Inc., "Frequently Asked Questions" Feb. 20, 2005. Online: www.splashpower.com.
Hui, S.Y.R., et al. "A New Generation of Universal Contactless Battery Charging Platform for Portable Consumer Electronic Equipment," *IEEE Transactions on Power Electronics*, May 2005, pp. 620-627, vol. 20, No. 3.
Tang, S.C., et al. "Evaluation of the Shielding Effects on Printed-Circuit-Board Transformers using Ferrite Plates and Copper Sheets," *IEEE Transactions on Power Electronics*, Nov. 2002, pp. 1080-1088, vol. 17, No. 6.
Tang, S.C., et al. "Characterization of Coreless Printed Circuit Board (PCB) Transformers," *IEEE Transactions on Power Electronics*, Nov. 2000, pp. 1275-1282, vol. 15, No. 6.
Tang, S.C., et al. "A Low Profile Power Converter Using Printed-Circuit-Board (PCB) Power Transformer with Ferrite Polymer Composite," *IEEE Transactions on Power Electronics*, Jul. 2001, pp. 493-498, vol. 16, No. 4.
Tang, S.C., et al. "Optimal Operation of Coreless PCB Transformer-Isolated Gate Drive Circuits with Wide Switching Frequency Range," *IEEE Transactions on Power Electronics*, May 1999, vol. 14, No. 3.
Fairchild Semiconductor, "Induction Heating System Topology Review," Jul. 2000, pp. 1-28.
Tsai, Huan-Shang et al. "Investigation of Current Crowding Effect of Spiral Inductors," *IEEE*, 1997, pp. 139-142.
Hui, Dong, et al. "Research on the Electromagnetic Radiation of a PCB Planar Inductor," *IEEE*, APMC2005 Proceedings, 2005.
Li, Faye, et al. "A Low Loss High-Frequency Half Bridge Driver with Integrated Power Devices using EZ-HV SOI Technology," *IEEE*, 2002, pp. 1127-1132.
Peter, M. et al. "Planar Inductors with Subdivided Conductors for Reducing Eddy Current Effects," *IEEE*, 2003, pp. 104-106.

* cited by examiner

| Description | Voltage (peak-peak) | Received Waveform |
|---|---|---|
| 9-turn, AWG-10 copper w/o shielding | 3.12Vp-p |  -f = 146kHz |
| 9-turn, AWG-10 copper w/shielding | 1.32Vp-p |  -f = 146kHz |
| 13-turn, AWG-10 copper coil w/ shielding | 3.44Vp-p |  -f = 147kHz |
| 10-turn, AWG-10 copper coil w/ shielding | 2.36Vp-p |  -f = 142kHz |
| Ferromagnetic 7.5cm diameter octagon | 23.5Vpp | 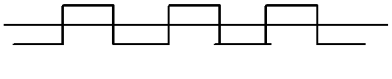 -f = 146kHz |
| 15-turn PCB coil, with 15mil traces. | 6.32Vp-p |  -f = 146kHz |
| 80-turn, AWG-14 copper coil w/ shielding | 3.40Vp-p |  -f = 146kHz |
| 15-turn coil, AWG-24 copper w/ shielding | 3.4Vp-p |  -f = 146kHz |
| -33-turn coil, 22-gauge magnet wire (enamel covered solid-conductor copper) | See graph for extended testing |  -f = 146kHz |

FIG. 34

METHOD AND APPARATUS FOR WIRELESS POWER TRANSMISSION

CROSS-REFERENCE TO RELATED APPLICATION

The present application claims the benefit of U.S. Application Ser. No. 60/844,478, filed Sep. 14, 2006, which is hereby incorporated by reference herein in its entirety, including any figures, tables, or drawings.

BACKGROUND OF THE INVENTION

In an increasingly mobile world, consumers have quickly embraced wireless technologies such as WiFi and Bluetooth to make their workspace less cluttered and more convenient. In order to power an ever growing assortment of battery operated devices, a consumer must deal with a large collection of bulky transformers and an unsightly, frustrating wire nest. Mobile users and travelers are often forced to lug a tangle of chargers and they often suffer for leaving one behind. In front of a cheering audience at the All Things Digital conference on Jun. 1, 2006, Martha Stewart brought a jumbled mess of power adapters to the microphone and challenged the tech community to find a solution [22].

There have been several attempts to bring a wireless power solution to consumers. The most common wireless systems charge our electric toothbrushes and razors. Two newer technologies, by SplashPower and Dr. Ron Hui of City University of Hong Kong, have also been presented.

Many electric toothbrushes and razors employ a voltage reducing transformer with no metallic contact between the primary and secondary side. For the efficiency of power transfer, designers typically incorporate ferromagnetic cores that provide a low reluctance path for magnetic fields traveling from the primary 100 to the secondary 110 windings, as illustrated in FIGS. 2A, 2B, and 2C. However, devices typically need to be placed in a very specific position or orientation with respect to the base station to be charged efficiently, or to be charged at all. In addition, the physical dimensions, such as the depth and weight of the components, can often make this system unsuitable for today's lightweight portable electronic devices.

SplashPower, founded by two Cambridge University students in June 2001, has disclosed a system that uses two perpendicular coils to create an even magnetic field distribution over a planar surface, as shown in FIG. 3. The coils alternate switching on and off to create two perpendicular magnetic fields, parallel to the base stations surface. When a device with a secondary winding having a highly permeable core is placed on the base station, magnetic fields will tend to travel through the low reluctance core rather than the surrounding air as shown in FIG. 4. FIG. 4 shows cross sectional views of SplashPower base station illustrating magnetic field lines (1), where the top figure shows undisturbed (no device present) field lines during normal operation and the middle figure shows the effect of placing a piece of ferromagnetic material (800) in the magnetic fields. The field lines can be seen traveling through the core rather than the surrounding air. The bottom figure simulates two individual cores in the magnetic field. Again, the magnetic fields travel through the core material rather than surrounding air. SplashPower indicates that specially equipped electronic devices can receive charge in any position or orientation on top of the base station. The SplashPower design has receivers built to include a dense ferromagnetic core, which would add undesirable bulk to small devices. As the SplashPower base station uses a two coil layout, it may waste large amounts of power, especially if a user attempts to charge a device in the corner of the pad. SplashPower's base station can be thick and clunky due to the inclusion of a dense ferromagnetic core.

Dr. Ron Hui, Chair Professor of Hong Kong City University's Department of Electronic Engineering, has disclosed a wireless power system having a transmitter claimed to create an even magnetomotive force in the immediate vicinity, by using a three layer array of hexagonal inductive coils, as shown in FIG. 5. FIG. 6 shows an mmf scan of a single layer, while FIG. 7 shows an mmf scan of the three layers. The inductive coils are coreless to allow a small, lightweight, low cost system. A receiving coil placed on top of the transmitter as shown in FIG. 5 can be used to charge an electronic device. However, interactions between multiple layers may hinder system performance, and the fabrication of multilayer PCB boards is considerably more expensive than single layer boards.

There is a need for a method and apparatus to reduce, or even eliminate, the need for a myriad of power supplies and wires in an efficient manner.

SUMMARY OF THE INVENTION

Embodiments of the invention relate to a method and system for transferring power wirelessly to electronic devices. The system can utilize magnetic coupling between two coils at close proximity to transfer sufficient power to charge an electronic device. Embodiments of the invention pertain to an array of spiral coils that can be used to transmit power for transfer to receiver coils. Potential applications of this technology include charging consumer electronic devices (cell phones, laptops, PDAs, etc), developing hermetically sealed devices for extreme environments, and less invasive transcutaneous energy transfer (TET) systems. Various embodiments of the subject system can be referred to as PowerPad system. Embodiments can incorporate one or more of the following: planar inductors, PCB transformers, and very high frequency power supplies. Embodiments of the invention also pertain to planar inductors, and/or arrays of planar inductors, having characteristics that allow the production of an even magnetic field, as well as systems that incorporate such planar inductors.

An embodiment of the PowerPad system can include two primary components: a base station, which can be referred to as PowerPad, and one or more receivers, which can be referred to as Power Mate. An embodiment of the base station is a planar device that provides power to the receiver modules. The PowerPad can simultaneously power multiple devices of different make, model, and power configuration placed in any position or orientation on its surface. The PowerPad can utilize an array of inductive coils attached to one or more high frequency power supplies. The PowerPad can be, for example, scaled to cover an entire desktop or integrated into an airplane tray table. Embodiments of the PowerPad can provide sufficient power to operate laptops, flat panel monitors, PDAs, cell phones, mp3 players, and other consumer electronic devices.

The receiver, which can be referred to as PowerMate, can be integrated into the chassis of an electronic device and can receive charge from the PowerPad. PowerMate is a relatively simple, low-cost receiving device designed to work in conjunction with the PowerPad. Devices equipped with a PowerMate unit receive power by being placed anywhere, directly on top of a PowerPad base station. To enable easy integration, the PowerMate can be small and lightweight. The device is scalable to satisfy the requirements of larger more power hungry devices. In an embodiment, a unit 1 mm thick and 36 mm in diameter is utilized and can receive more than enough power to drive a laptop computer or flat panel monitor.

BRIEF DESCRIPTION OF THE DRAWINGS

The patent or application file contains at least one drawing executed in color. Copies of this patent or patent application publication with color drawing(s) will be provided by the Office upon request and payment of the neccessary fee.

FIG. 34 shows a received waveform of an embodiment of the PowerMate produced under indicated coil and voltage conditions.

DETAILED DESCRIPTION OF THE PREFERRED EMBODIMENT

Embodiments of the invention relate to a method and system for transferring power wirelessly to electronic devices. The system can utilize magnetic coupling between two coils at close proximity to transfer sufficient power to charge an electronic device. Embodiments of the invention pertain to an array of spiral coils that can be used to transmit power for transfer to receiver coils. Potential applications of this technology include charging consumer electronic devices (cell phones, laptops, PDAs, etc), developing hermetically sealed devices for extreme environments, and less invasive transcutaneous energy transfer (TET) systems. Various embodiments of the subject system can be referred to as Power Pad system. Embodiments can incorporate one or more of the following: planar inductors, PCB transformers, and very high frequency power supplies. Embodiments of the invention also pertain to planar inductors having characteristics that allow the production of even magnetic field, as well as systems that incorporate such planar inductors.

Figure 1:
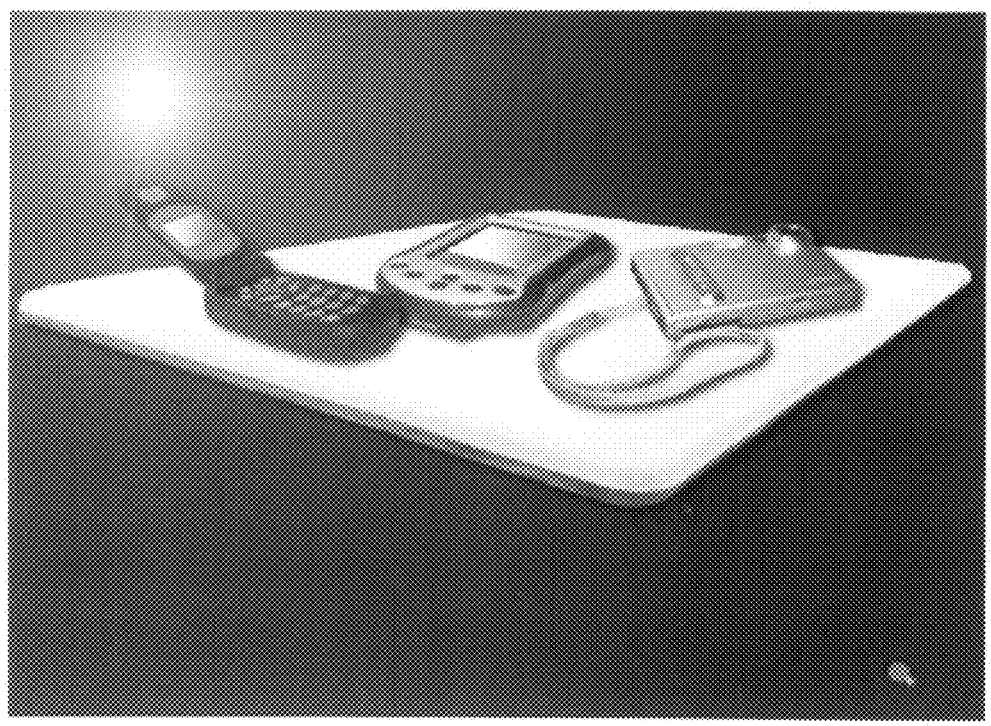
FIG. 1 shows an embodiment of Power Pad System.
Figure 2A:
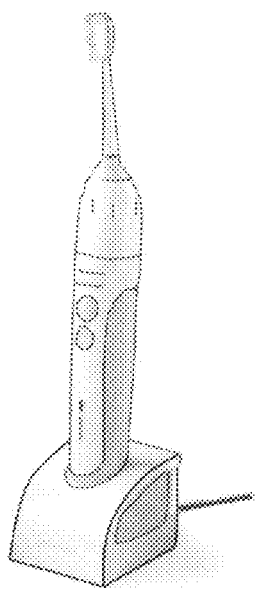
FIGS. 2A-2C show wireless technology used in electric toothbrushes and razors, where ferromagnetic cores are at the center of each winding and magnetic fields created by the bottom winding (base) induce current in the top winding (device).
Figure 2B:
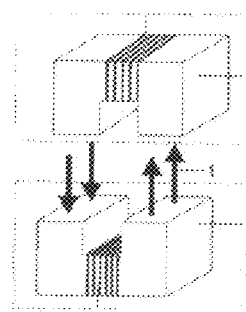
Figure 2C:
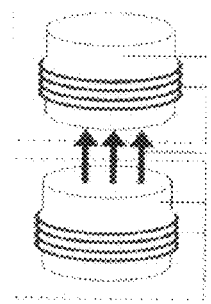
Figure 3:
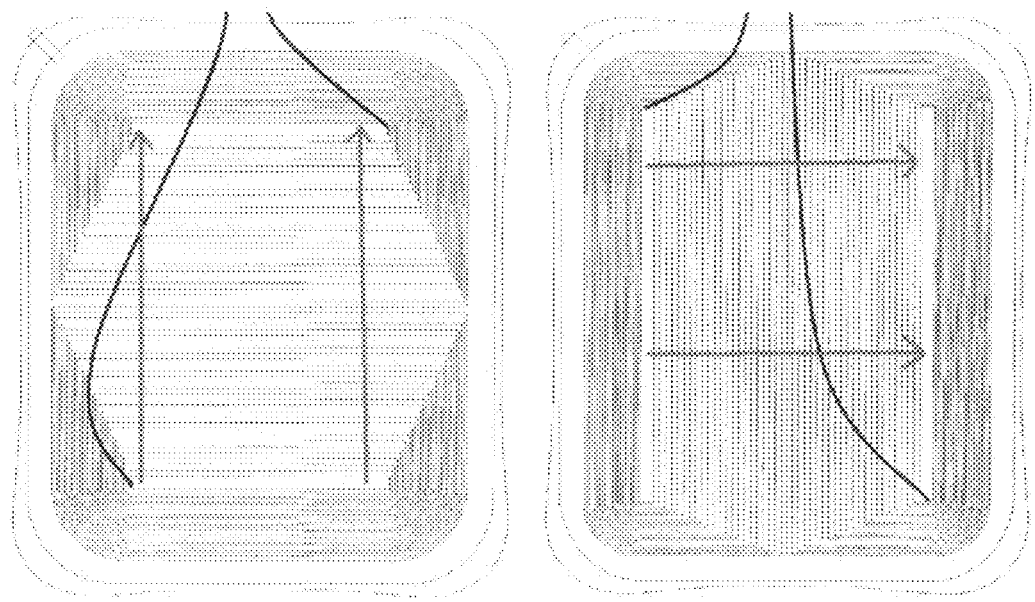
FIG. 3 shows a top down view of the two coils in the SplashPower base station where magnetic fields directions are shown as large arrows.
Figure 4:
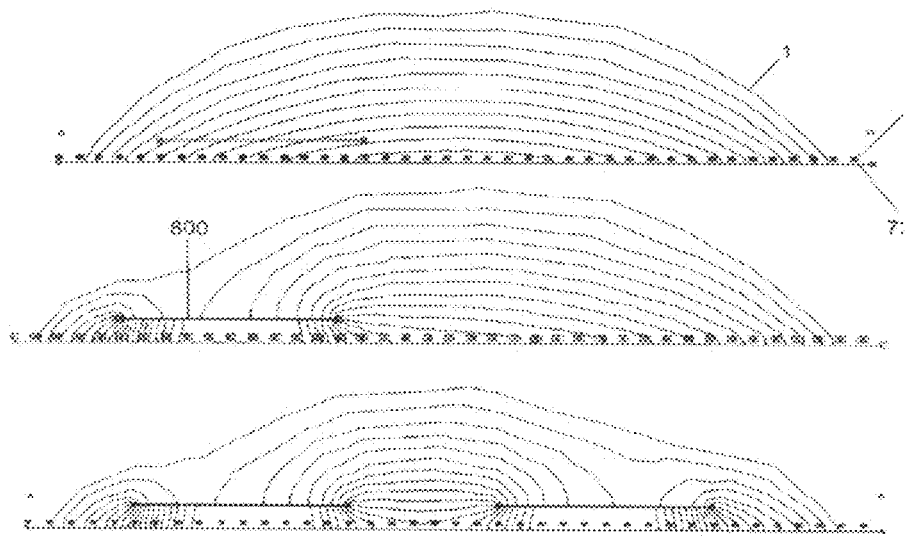
FIG. 4 shows magnetic field patterns for a SplashPower base station.
Figure 5:
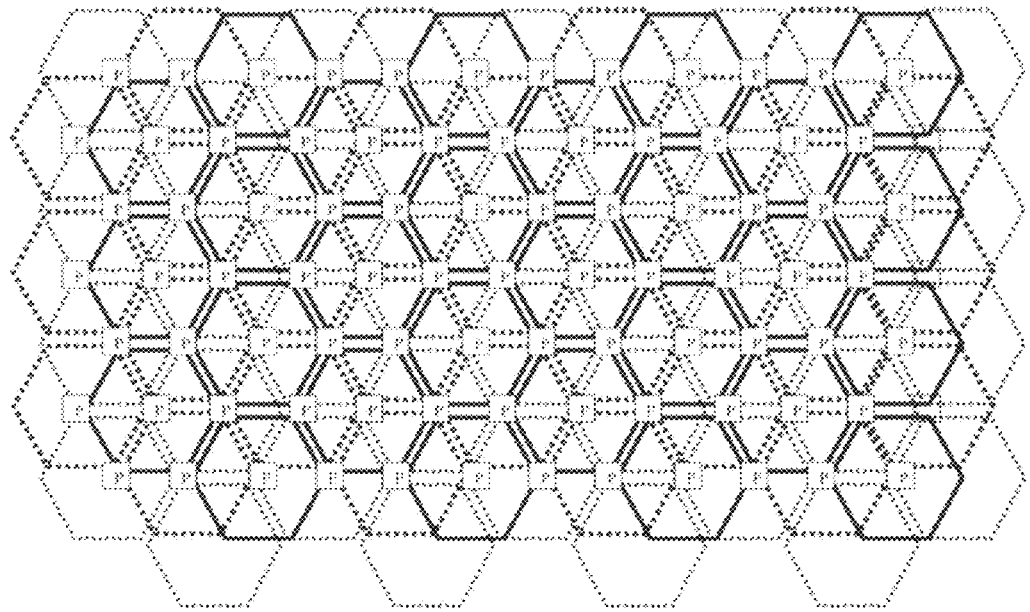
FIG. 5 shows a structure of three-layer hexagonal array.
Figure 6:
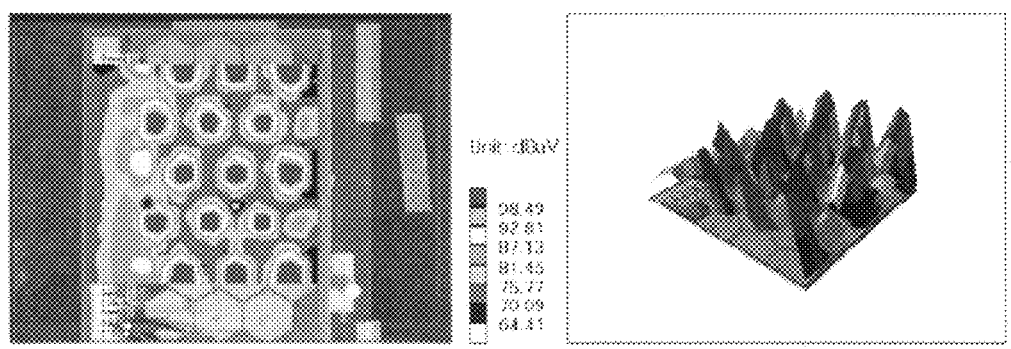
FIG. 6 shows an mmf scan for a single layer design having an uneven magnetic field.
Figure 7:
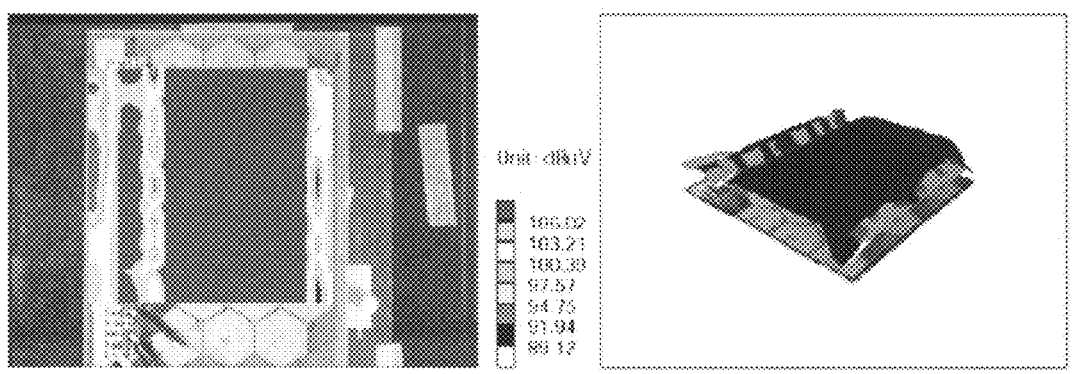
FIG. 7 shows an mmf scan for three layer design, where the distribution of magnetic fields improves considerably, compared to the distribution of FIG. 6.

FIG. 1 shows an embodiment of a PowerPad system in accordance with the subject invention. An embodiment of the PowerPad system can include two primary components: a Base Station, which can be referred to as PowerPad, and one or more receivers, which can be referred to as PowerMate. An embodiment of the base station is a planar device that provides power to the receiver modules. The PowerPad can simultaneously power multiple devices of different make, model, and power configuration placed in any position or orientation on its surface. The PowerPad can utilize an array of inductive coils attached to one or more high frequency power supplies. The PowerPad can be, for example, scaled to cover an entire desktop or integrated into an airplane tray table. Embodiments of the Power Pad can provide sufficient power to operate laptops, flat panel monitors, PDAs, cell phones, mp3 players, and other consumer electronic devices. M. Peter, H. Hein, F. Oehler, P. Baureis, "Planar Inductors with Subdivided Conductors for Reducing Eddy Current Effects," IEEE, 2003 provides an overview of existing technologies, discusses operational theory applicable to embodiments of the Power Pad system, and is hereby incorporated by reference in its entirety.

The receiver, which can be referred to as PowerMate, can be integrated into the chassis of an electronic device and can receive charge from the PowerPad. The PowerMate is a relatively simple, low-cost receiving device designed to work in conjunction with the PowerPad. Devices equipped with a PowerMate unit receive power by being placed anywhere, directly on top of a PowerPad base station. To enable easy integration, the PowerMate can be small and lightweight. The device is scalable to satisfy the requirements of larger more power hungry devices. In an embodiment, a unit 1 mm thick and 36 mm in diameter is utilized and can receive more than enough power to drive a laptop computer or flat panel monitor.

In an embodiment, devices can be placed on the pad in any orientation. Without the need to carefully position the device or fumble with adapters. The PowerPad can eliminate power cables for all types of electronic devices, and eliminate the associated unsightly wire nests. An embodiment of the Power Pad is a versatile device capable of providing power to almost any type of electronic device. Power Pad can charge multiple devices at once as if they were plugged into their conventional adapters. Embodiments of the Power Pad can be integrated into desks, tables, and other flat surfaces. Users can take their devices to the coffee shop, lecture hall, or an airplane and charge their devices on PowerPad enabled surfaces. Electronic device manufacturers can integrate the subject technology into their devices.

Figure 8:
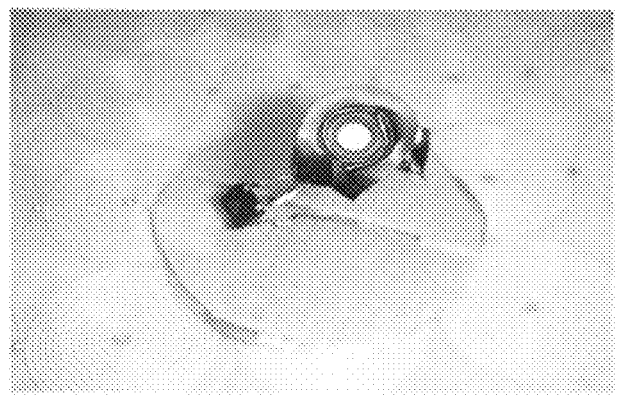
FIG. 8 shows an embodiment of a PowerMate module driving an LED on top of an embodiment of a Power Pad surface.

Embodiments of the subject system utilize PCB transformers, which incorporate polychlorinated biphenyls (PCB's). Embodiments of the invention utilize multiple layers of coils for generation of magnetic fields. An LED equipped with a PowerMate receiver module, in accordance with an embodiment of the invention, as shown in FIG. 8, reliably illuminated when placed in any position or orientation on top of an embodiment of the PowerPad's surface.

In order to charge devices placed in various locations on its surface, and in a specific embodiment anywhere on its surface, an embodiment of the PowerPad base station generates an even high frequency, magnetic field. The PowerMate receiver converts this magnetomotive force into electrical current and supplies power to, for example, an electronic device.

Figure 9:
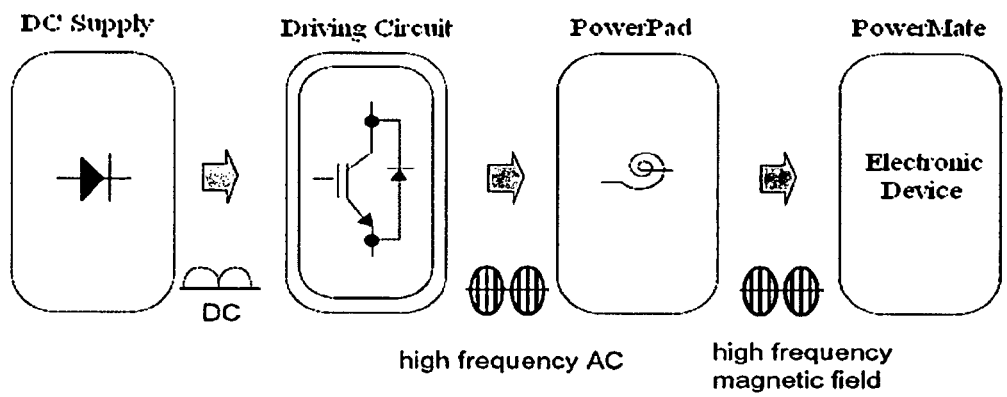
FIG. 9 shows a PowerPad system block diagram for a specific embodiment in accordance with the subject invention.
Figure 10:
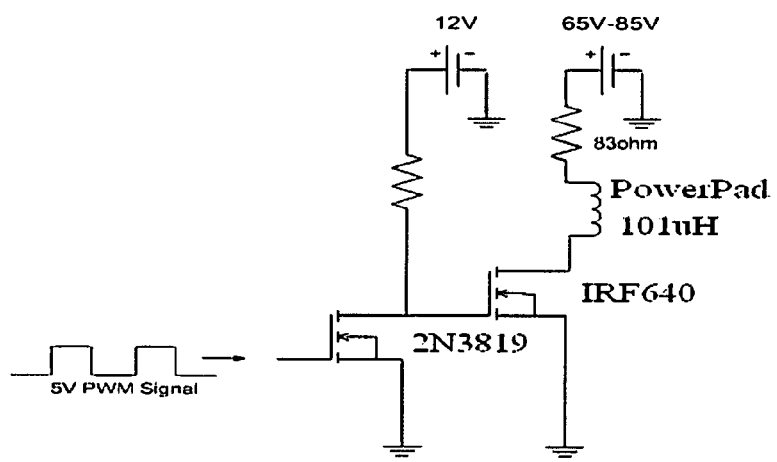
FIG. 10 shows a driving circuit used in an embodiment of a PowerPad.

A specific embodiment of the invention has four primary components and will be described with reference to FIG. 9. A DC power supply 310 uses three 1A, 13.5/30V RadioShack power supplies connected in series to produce a 65V output. During steady-state operation the entire system draws a maximum of 0.65 amps. A microprocessor controlled driving circuit 330 includes two cascaded resistive load switches, as shown in FIG. 10. A PIC12F629 8-pin microprocessor switches a 2N3819 n-channel MOSFET at 208 kHz. The drain terminal of the 2N3819 MOSFET drives the gate of a larger IRF640 power MOSFET. The output is a 65 Vpp, 208 kHz square wave output that feeds into the PowerPad base station.

Figure 11:
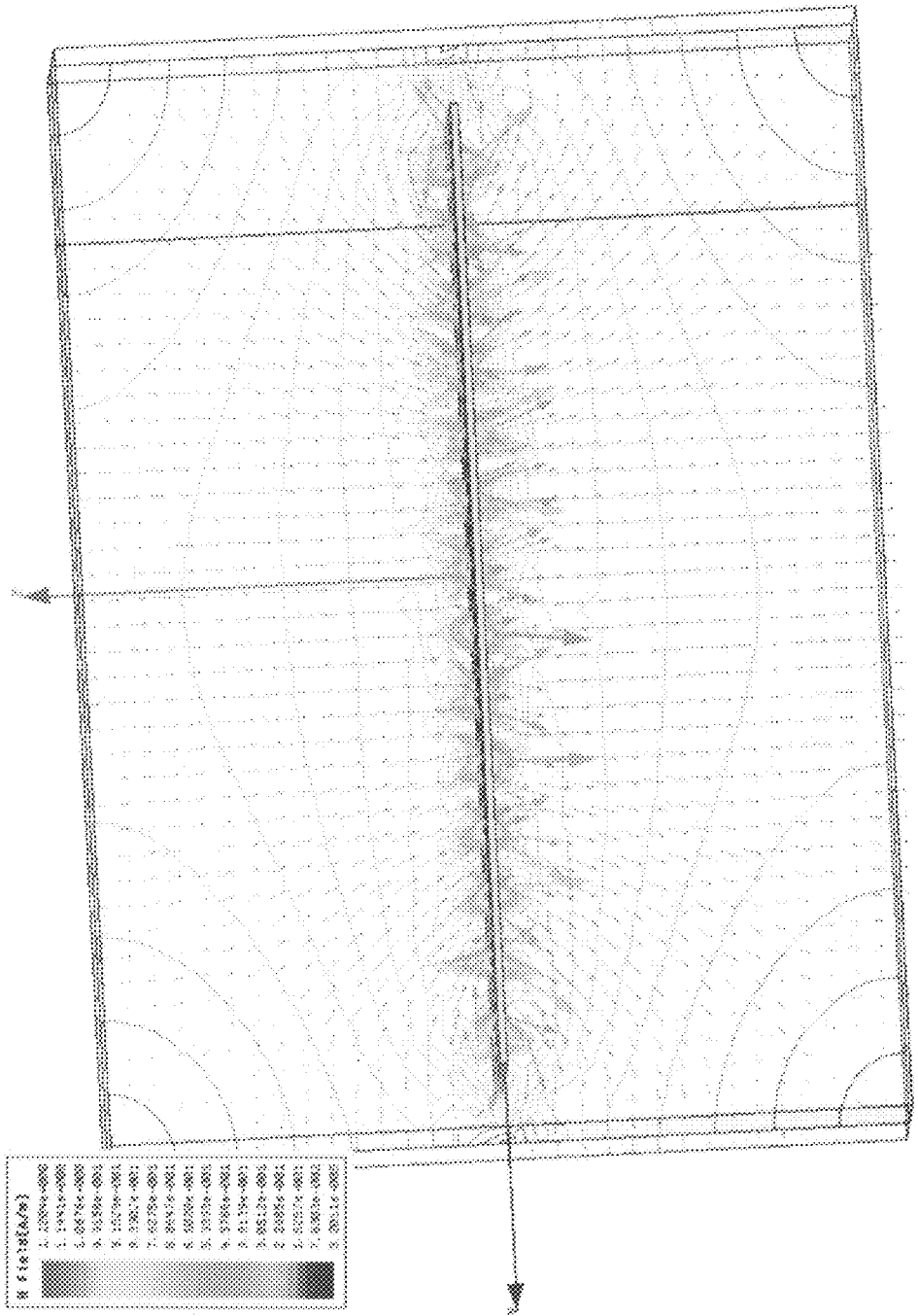
FIG. 11 shows a Magnetic field (H Field) vector and magnitude plot for a spiral inductor cross-section having an uneven field distribution with peak fields in the center and minimum fields on the perimeter.
Figure 12:
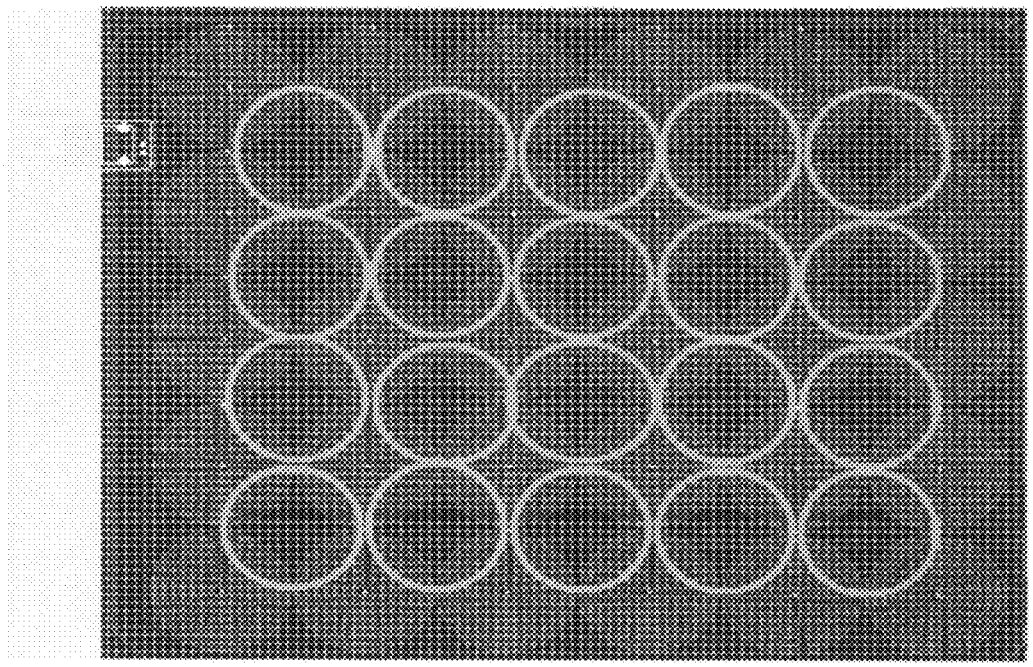
FIG. 12 shows a Protei layout of a top layer, where the location of the bottom layer is drawn in light circles.

Magnetic field vector and magnitude field plots of spiral inductor cross-sections are shown in FIG. 11, and reveal peak intensity at the center of the inductor and minimum intensity along the perimeter. To compensate for this phenomenon, a second layer of inductors can be arranged, as shown in FIG. 12, such that the peak magnetic field regions of the bottom layer align with minimum magnetic field regions of the top. The embodiment of the PowerPad shown in FIG. 12 uses a two layer, series connected, array of PCB, spiral inductors to create an even magnetic field over its surface. Inductors are arranged in series so that current does not bypass the loaded region of the Power Pad. The inductors are 15 turn inductors with 15 mil trace widths and 25 mil trace gaps.

Figure 13:
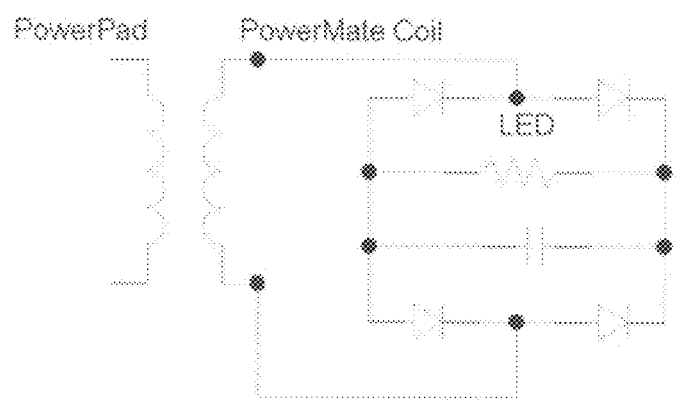
FIG. 13 shows a schematic for an embodiment of a PowerMate.

The receiving device for this embodiment includes a 33 turn, 22 gauge magnet wire coil connected to a full bridge rectifier. Current flows from the rectifier into a parallel connected LED and 220 capacitor, as shown in FIG. 13. Table 4.1 shows the system specifications for a specific embodiment of the invention.

TABLE 4.1

System Specifications

| | Parameter | Description |
|---|---|---|
| 1 | PowerPad Transmission Region | Planar, 19.5 cm*16 cm |
| 2 | Max Received Power | 3.7 VDC, and 2.4 mA, ~10 mW |
| 3 | PowerMate Diameter | 6 cm |
| 4 | PowerMate Weight | 14 grams |
| 5 | Transmission Range | <1 cm |
| 6 | Input Voltage/Current | 65 VDC, 0.65 A ~40.3 Watts |
| 7 | Voltage Fluctuation above Transmission Region | 17.5% |
| 8 | Efficiency | .025% |

Figure 14:
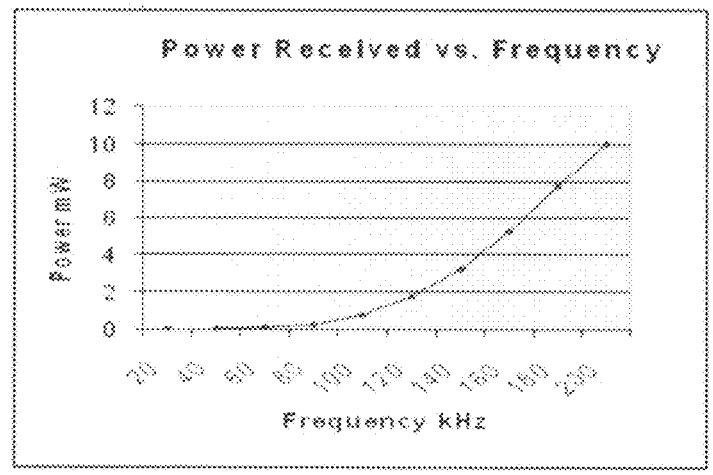
FIG. 14 shows the received power vs. driving circuit frequency for an embodiment of the subject invention.

Increasing the DC supply voltage can yield proportional gains in received power. With respect to frequencies from 0 to 200 kHz, a higher frequency can result in more efficient coupling, as shown in FIG. 14, which shows received power vs. driving circuit frequency.

Figure 15:
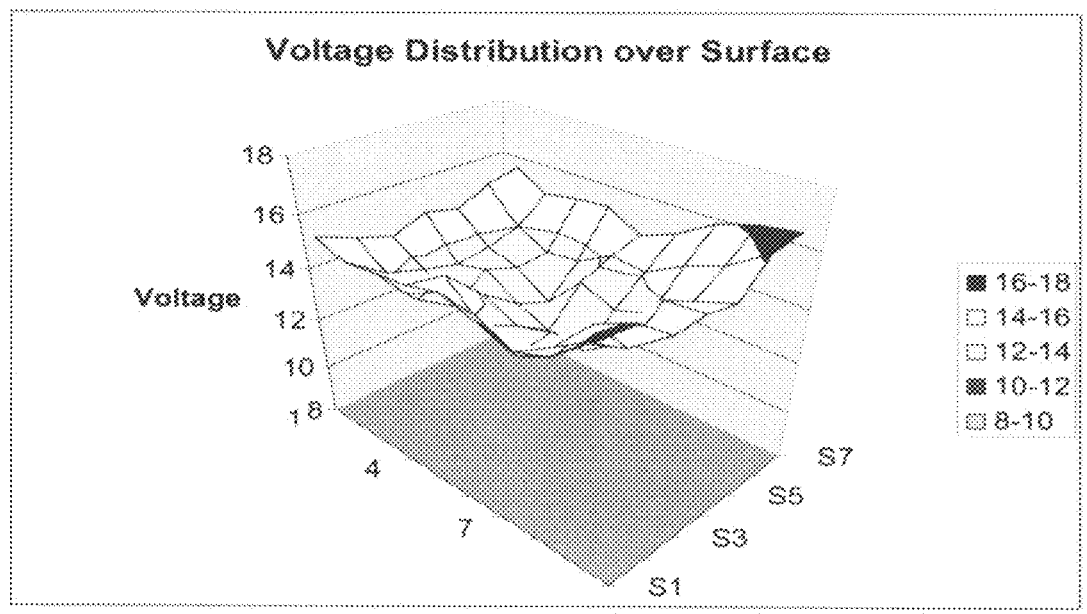
FIG. 15 shows a relative voltage distribution over the surface of an embodiment of the PowerPad.

Probe measurements above an embodiment of the Power Pad reveal peak voltages around the perimeter and lower voltages in the center, as shown in FIG. 15, which shows a relative voltage distribution over the surface of the PowerPad. The low voltage region is likely attributable to destructive interference between the top and bottom layer inductor arrays.

With respect to embodiments of the PowerMate, inline with theoretical expectations, large coils with many turns received the most power. Increasing the spacing between conductors significantly reduced the received power. A large number of designs were evaluated. The results are shown in FIG. 34 which illustrates a table including test results of the PowerMate with PowerPad input of: 146 kHz; 130 Vp-p, 50% duty cycle, square wave. A specific embodiment of the PowerMate, listed last in the table of FIG. 34, uses a 33 turn, 22 gauge magnet wire coil.

The resistive load configuration of an embodiment of a driving circuit dissipated 18.4 watts of power as heat loss and delivered 55% of the input power to the PowerPad. The heat byproduct can be addressed with several large heat sinks and fans to regulate the temperature of the prototype.

Figure 16:
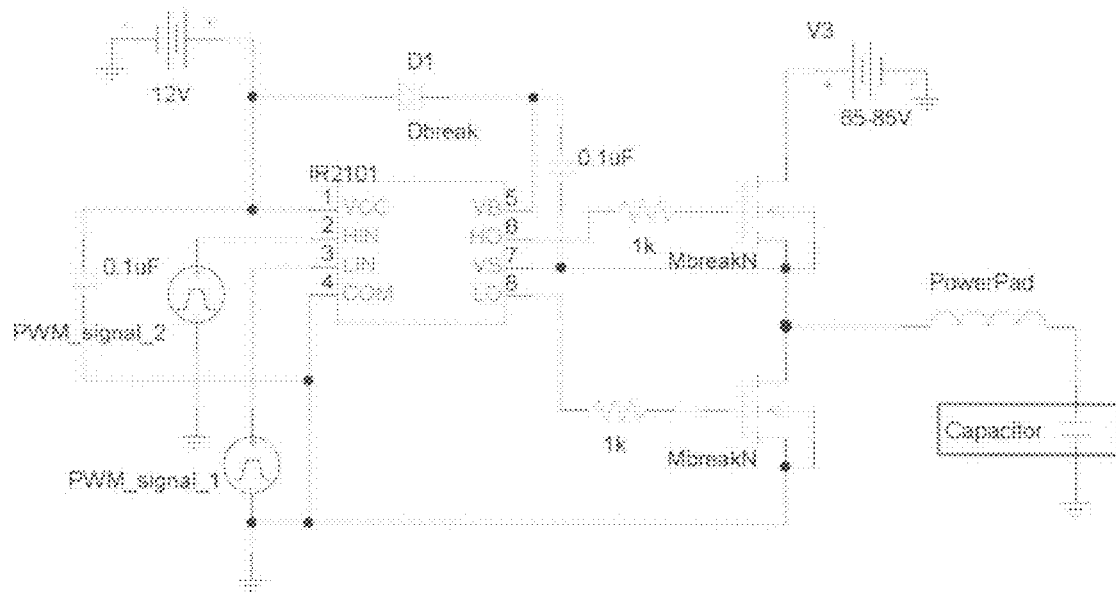
FIG. 16 shows a microprocessor controlled half bridge inverter that can be utilized in accordance with an embodiment of the subject PowerPad.

Another embodiment, having a circuit employing a microprocessor controlled, halfbridge inverter, as shown in FIG. 16, is designed without resistive elements and significantly reduces the wasted power. Referring to FIG. 16, a microprocessor transmits two high frequency signals, 180 degrees out of phase, to the high and low side inputs of an IR21 01 gate driver. The gate driver switches two n-channel MOSFETs that create a high frequency, 65V square wave feeding into the PowerPad base station. This driving circuit delivered ~95% of the input to the PowerPad and significantly reduced the cooling requirement.

Figure 17:
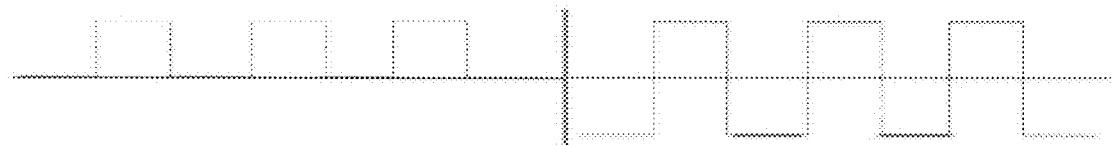
FIG. 17 shows a voltage waveform measured across the PowerPad terminals before and after insertion of the capacitor shown in FIG. 16.

The half-bridge inverter design permits the insertion of a capacitor between the PowerPad and ground, as shown in FIG. 16. This addition can double the peak to peak voltage by pumping charge back through the PowerPad as it is switched from 65 volts to ground, as shown in FIG. 17, which shows a voltage waveform measured across the PowerPad terminals before and after insertion of the capacitor shown in FIG. 16.

Figure 18:
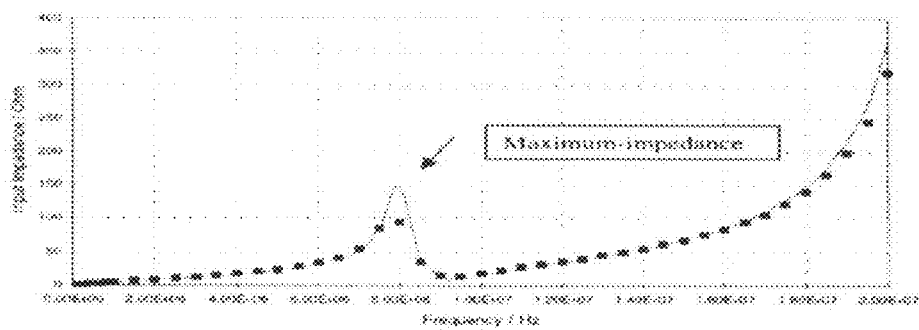
FIG. 18 shows impedance vs. frequency for a PCB transformer.
Figure 19:
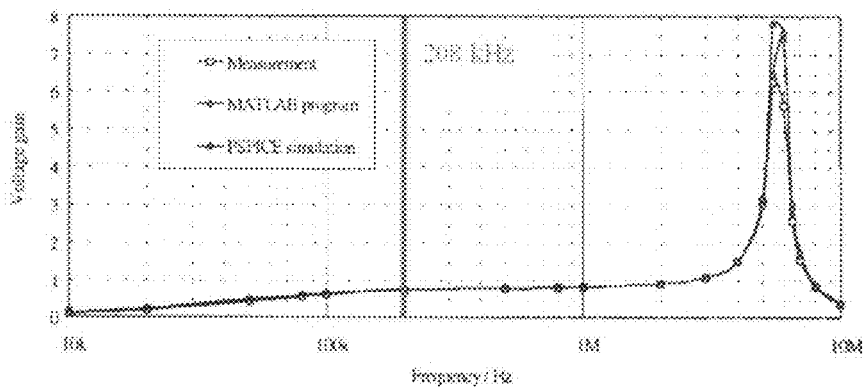
FIG. 19 shows voltage gain vs. frequency for a PCB transformer.

The resonant frequency of typical core less PCB transformers is between 1 and 10 MHz [5]. At much lower frequencies, the primary windings behave like a short circuit and dissipate a large amount of power. Studies have shown that voltage gain is highest and power transfer is most efficient, at the maximum impedance frequency, as illustrated in FIG. 18 and FIG. 19, where FIG. 18 shows impedance versus frequency for a PCB transformer, and FIG. 19 shows voltage gain versus frequency for a PCB transformer. The maximum impedance frequency is indicated in FIG. 18. Referring to FIG. 19, gain increases significantly at the maximum impedance frequency (208 kHz). The frequency of existing driving circuit is shown (208 kHz). At this ideal frequency, which is generally found immediately below the resonant frequency, 90% efficient embodiments of systems in accordance with the invention have been built and tested.

The PIC microprocessor used in an embodiment has a maximum stable output of 208 kHz, significantly lower than the optimum frequency range from FIG. 19. A microprocessor with a ~10 MHz switching capability can substantially improve efficiency. Switching losses in today's power electronics can become too large to operate efficiently beyond 10 MHz.

Figure 20:
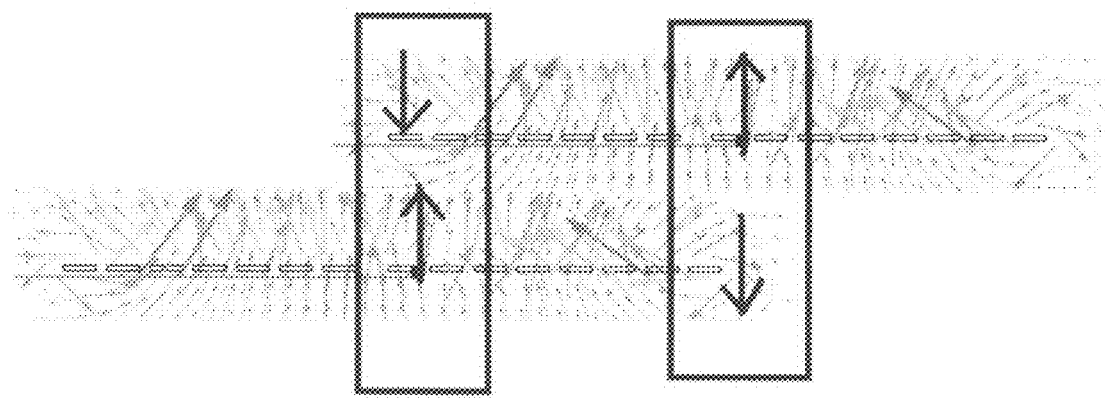
FIG. 20 shows Ansoft HFSS H field vectors that can be seen flowing in opposing directions, where the large arrows show a generalization of the net effect.
Figure 21:
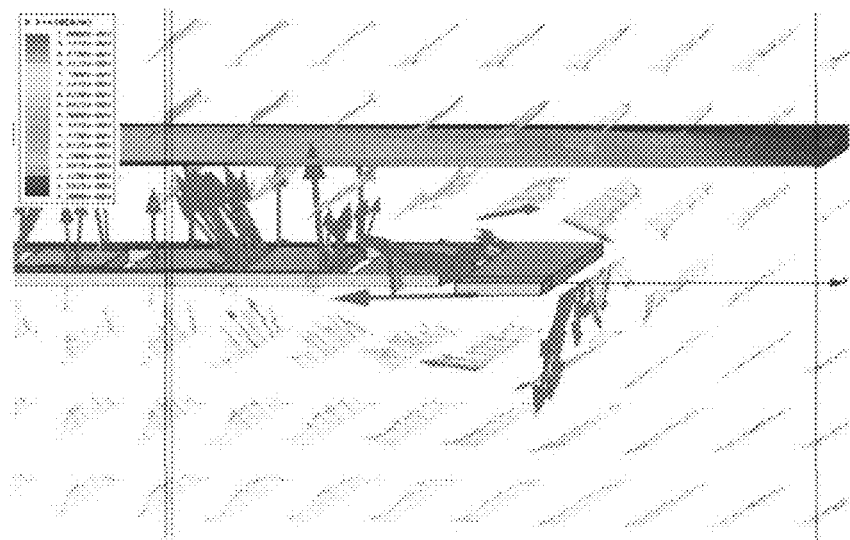
FIG. 21 shows a close up of the magnetic field vectors along the perimeter of a spiral inductor.

Simulations using Ansoft HFSS 3D electromagnetic simulation software provide better insight into the destructive interference patterns, as shown in FIG. 20, which shown Ansoft HFSS H field vectors that are flowing in opposing directions. The large arrows in FIG. 20 show a generalization of the net effect. Magnetomotive force peaks at the center of a planar inductor and is negative around the perimeter, as shown in FIG. 21, which shows a close up of the magnetic field vectors along the perimeter of a spiral inductor. Referring to FIG. 21, the fields at the perimeter are opposite in direction to the fields at the center. By layering and aligning coils as shown in FIG. 12 opposing magnetic fields are created thereby reducing coupling efficiency.

Figure 22:
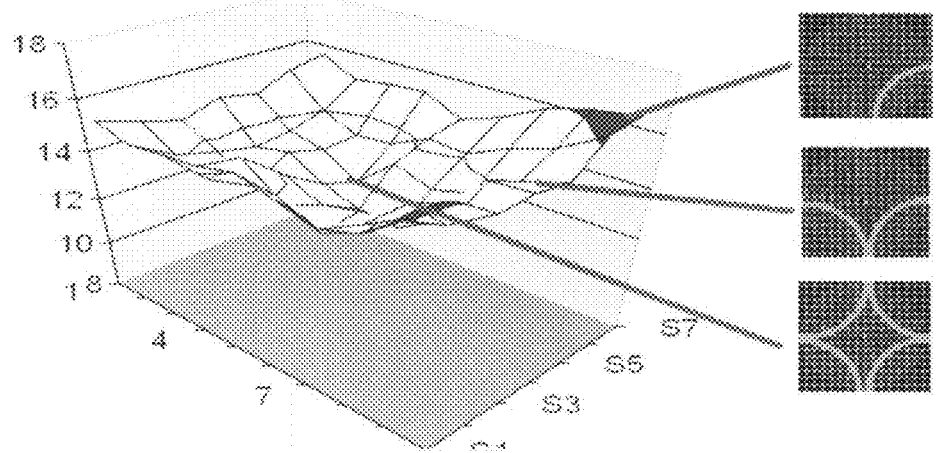
FIG. 22 shows a voltage distribution over the surface of a two layer array that shows coil overlap compared to received voltage.

Test data shows maximum voltages are located at the corners where coil overlap is minimal, medium voltages are found around the perimeter where overlap is moderate, and the lowest voltages occur in the center where inductor overlap is the greatest, as illustrated in FIG. 22, which shows a voltage distribution over the surface of a two layer array. FIG. 22 indicates that minimum overlap between layers results in maximum efficiency. An embodiment with a single layer of array coil may allow maximum efficiency.

Figure 23:
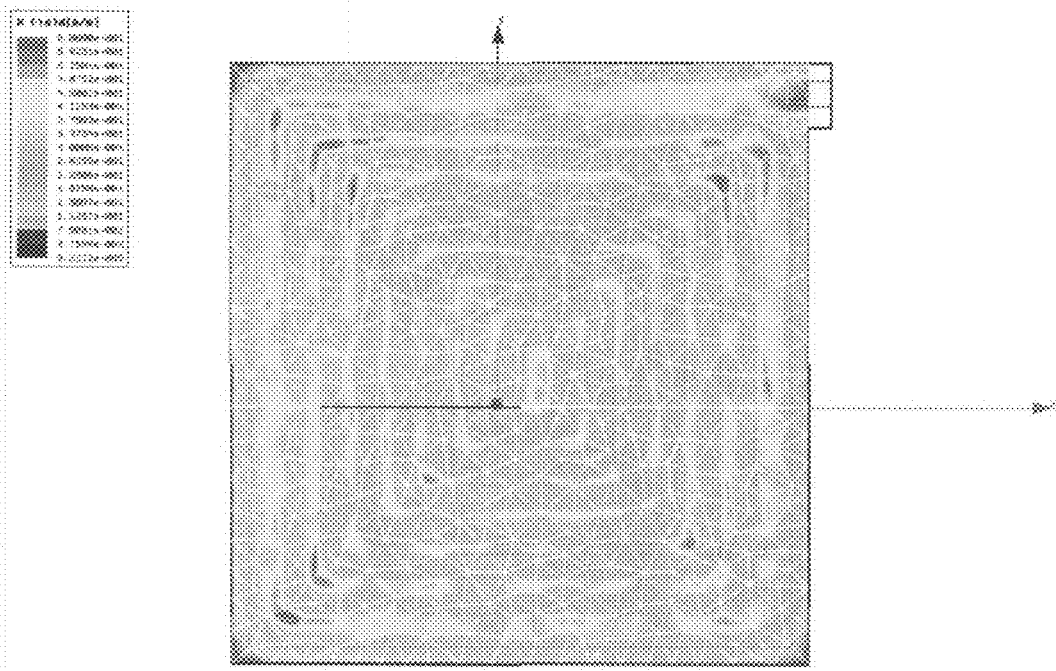
FIG. 23 shows the magnetic field intensity measured at 0.4 mm over a square inductive coil.

The inductive coils in an embodiment have a thin 15 mil trace width and a 25 mil trace gap. This arrangement was based on the assumption that current carrying traces obstruct magnetic fields and therefore, large trace separations would contribute to good inductive coupling as illustrated in FIG. 23, which shows the magnetic filed intensity measured at 0.4 mm over a square inductive coil. The magnetic fields have been blocked in the regions found immediately above the conducting traces.

Figure 24:
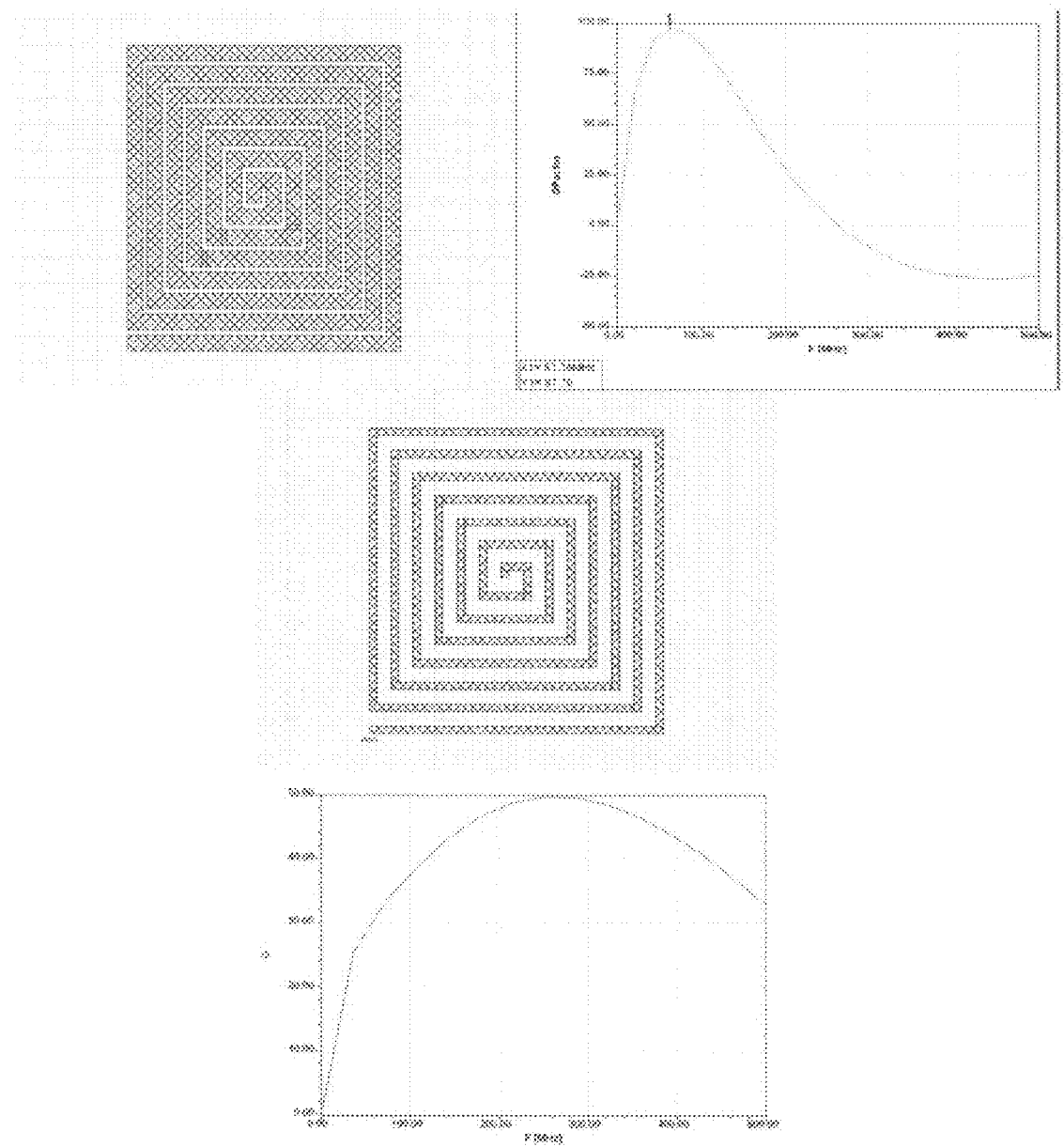
FIG. 24 shows the effect of trace width and spacing on Q factor.

In simulations, current carrying traces were found to block magnetic fields. However, a narrow trace spacing actually increases coupling efficiency. This can be verified by examining the quality factor of two inductive coils with identical areas and turns ratios, as shown in FIG. 24. FIG. 24 shows the Q factor for a thin trace and large trace gap spiral coil, which show a 50% lower quality factor for the thin trace width coil that is centered on a frequency too high for power electronics. The thin trace design has a much lower Q factor and resonated at frequencies too high for certain desired driving circuit designs. Embodiments of the invention can incorporate inductors where the traces are widened and the gaps are narrowed. The ratio of the trace to gap widths can be optimized for efficiency, or determined to meet other design criteria. In an embodiment, inter-winding capacitance can be neglected due to the relatively low operating frequency and the inductor's short overall conductor length.

In various embodiments, the inductors can have a square or hexagonal coil shape, to allow for a more efficient use of board space. Square and hexagonal inductors can be tiled with little wasted space. Other embodiments can have other shapes, such as a circular pattern.

Figure 25:
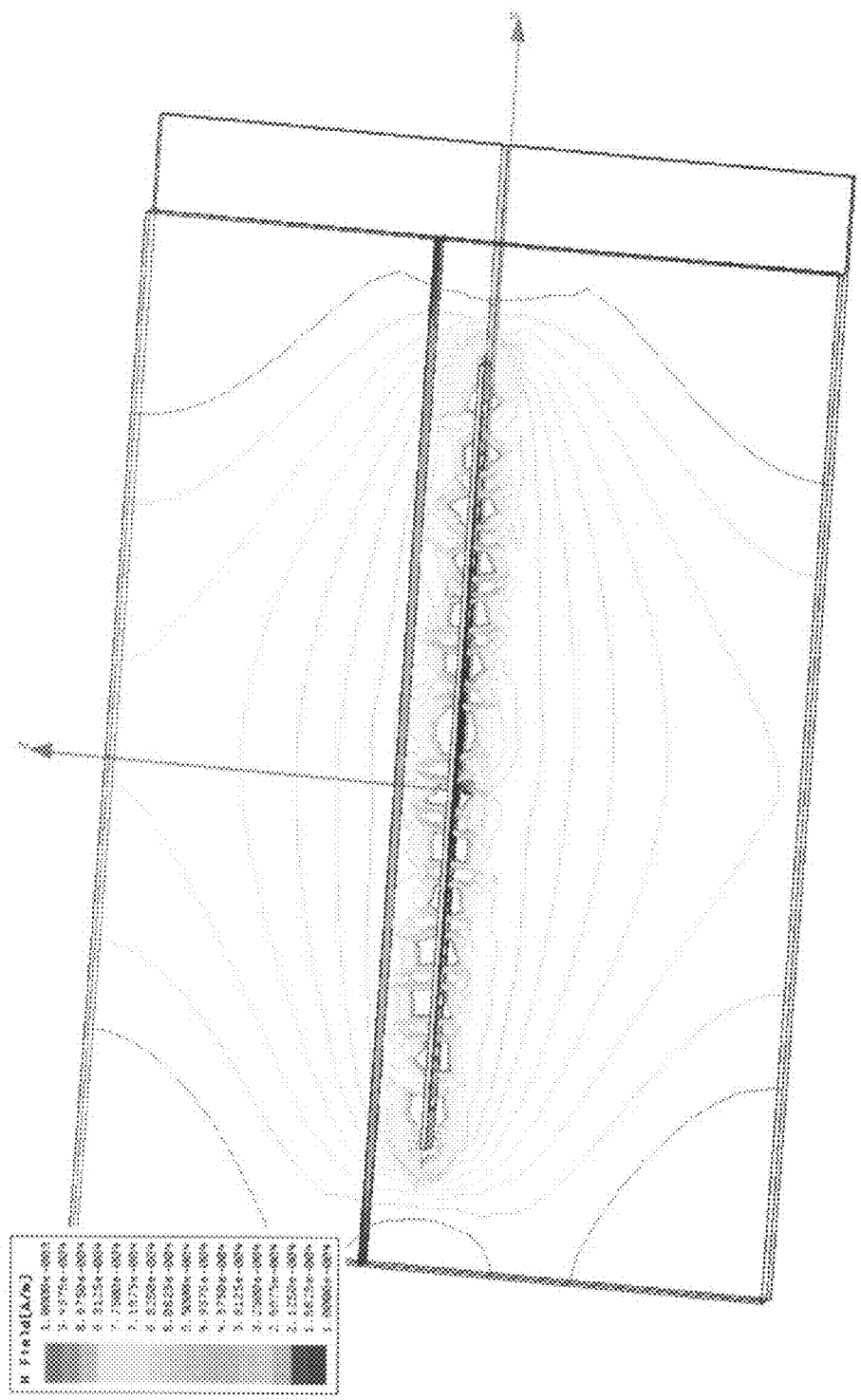
FIG. 25 shows the magnetic field distribution of a typical planar inductor, where the field peaks in the center.
Figure 26:
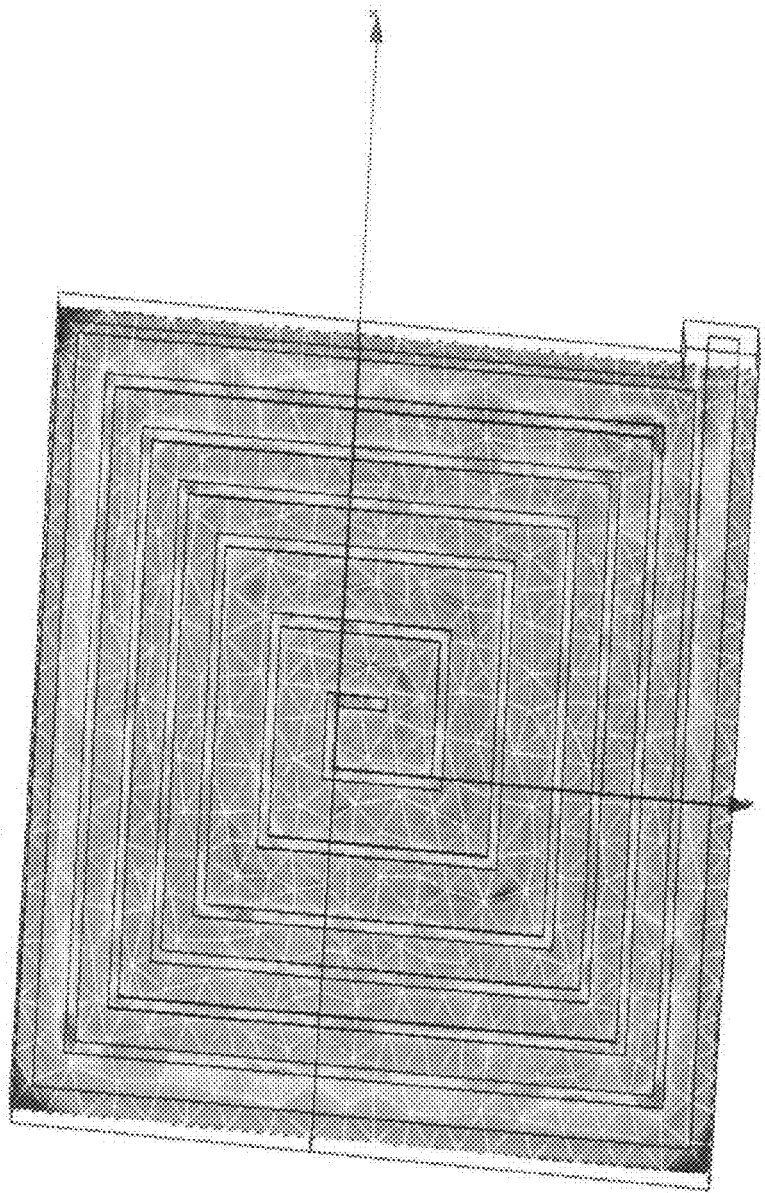
FIG. 26 shows the effect of variable width planar inductor on magnetic field.
Figure 26:
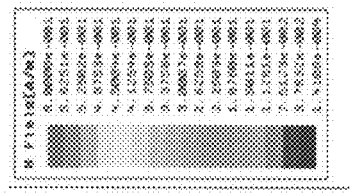

One drawback of certain embodiments with a single layer arrangement is an uneven magnetic field distribution, as shown in FIG. 25, which shows the magnetic field distribution of a typical planar inductor. The unevenness can be difficult to fully eliminate. The unevenness can be reduced by using traces that become thicker as they spiral towards the center. Thick current carrying traces at the center of the inductor can block the peak magnetic field for a more balanced field distribution, as shown in FIG. 26, which illustrates the effect of the variable width planar inductor on magnetic field. The wider conductor 200 in the middle is clearly limiting the magnetic field flux through that region. Additionally, thin perimeter 210 traces can reduce the size of the region of minimum field intensity.

Figure 27:
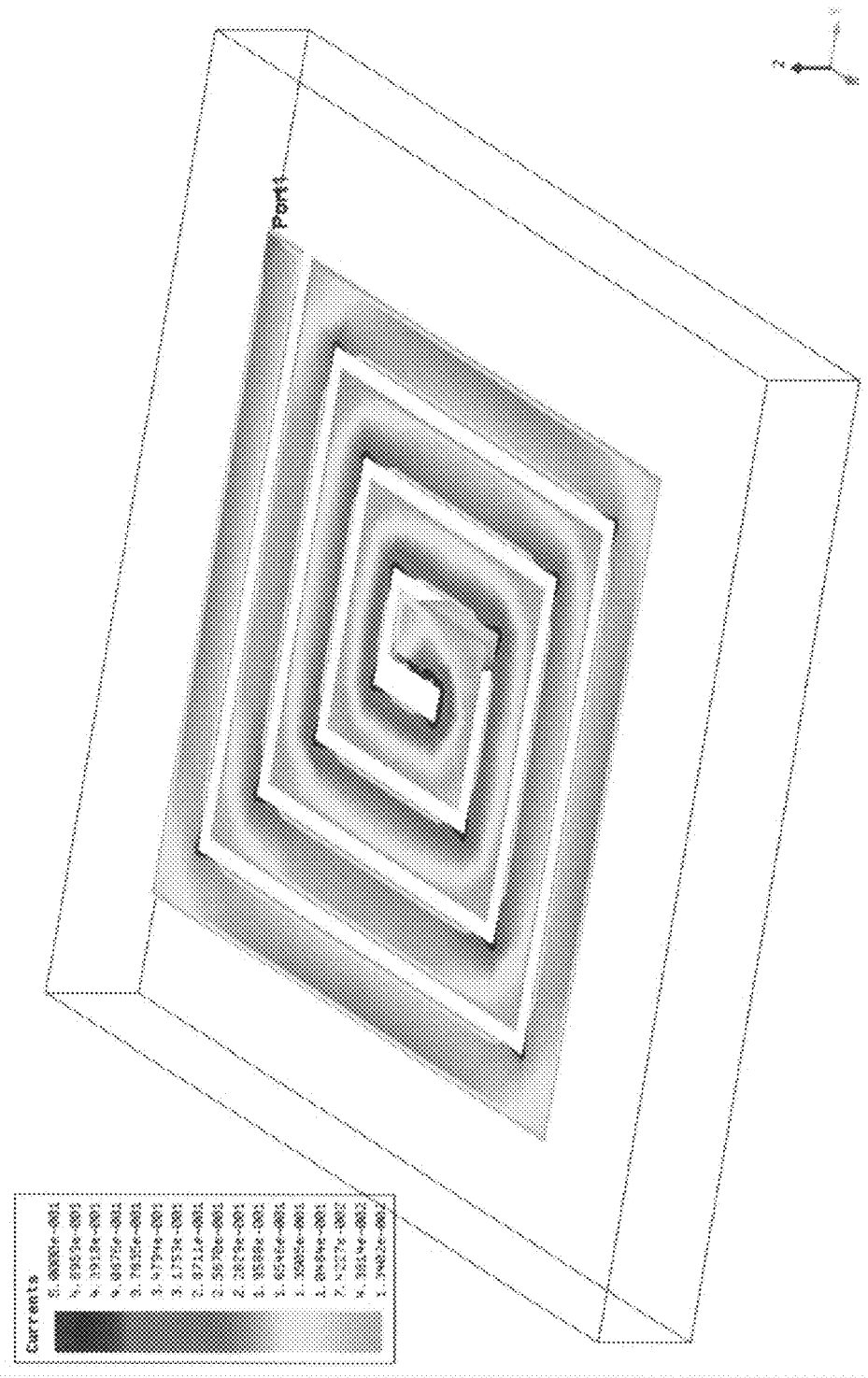
FIG. 27 shows the current crowding effect seen on a planar inductor.

The corners of a square inductor can begin to obstruct current beginning in the MHz range due to the current crowding effect [7]. Magnetic fields tend to push current distribution towards the center of the inductor, reducing the effective cross-sectional area of the conductor and thereby increasing resistance. This effect is seen throughout the conductor, but becomes especially dominate towards the center and at the corners as shown in FIG. 27, which shows the current crowding effect seen on a planar conductor. Note the very high current density at the corners in FIG. 27. Embodiments can involve smoothing the corners of the inductor so as to reduce the crowding effect resulting in reduced resistance and increased efficiency.

At high frequencies eddy currents can result in increased resistance and heat loss. A slotted conductor can disrupt these currents and increase the Q factor by up to 35% at frequencies around 2 GHz [11]. Embodiments of the subject invention can incorporate slotted conductors to improve efficiency.

Figure 28:
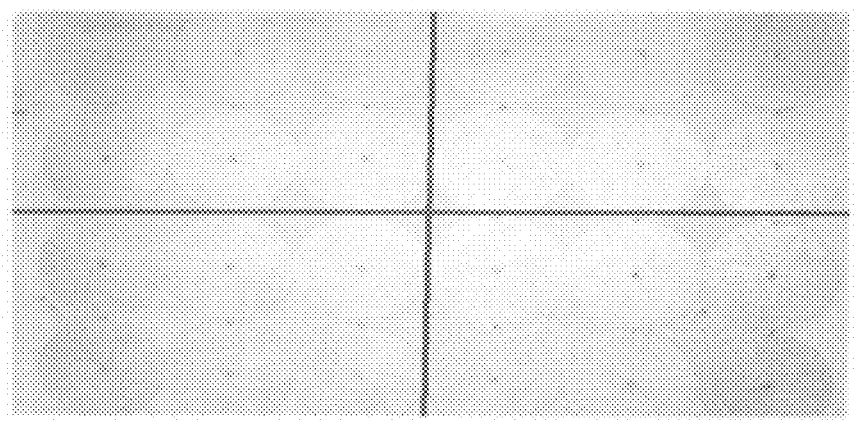
FIG. 28 shows an example of a subdivided embodiment of a PowerPad.
Figure 29:
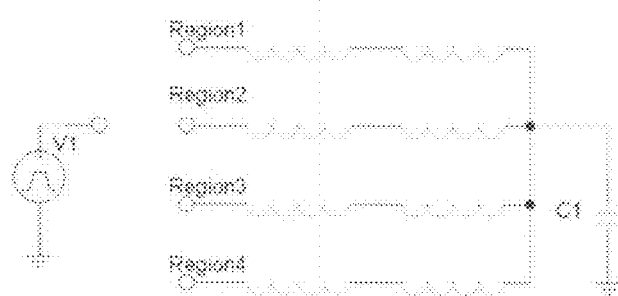
FIG. 29 shows an embodiment of a circuit schematic that can be utilized to drive the subdivided PowerPad layout shown in FIG. 2B.

An embodiment of an inductor array utilized in a PowerPad has an input resistance of 83 ohms due to the series connected arrangement of fifty spiral inductors. As discussed, a series arrangement ensures that current does not bypass loaded regions of the PowerPad. A series arrangement can result in a high input resistance and can result in the entire surface dissipating power even when only a small region is loaded. An embodiment can incorporate a hybrid arrangement of inductive coils. The coils can be grouped into separate regions that activate only when a load is present, as shown in FIGS. 28 and 29. FIG. 28 shows an embodiment divided into four regions with each region having six spiral conductors. FIG. 29 show an embodiment of a circuit that can be utilized to drive the subdivided PowerPad layout of FIG. 28. Depending on the load, dividing the array into four sections could quadruple the efficiency. Additional subdivisions can further increase the efficiency.

Figure 30:
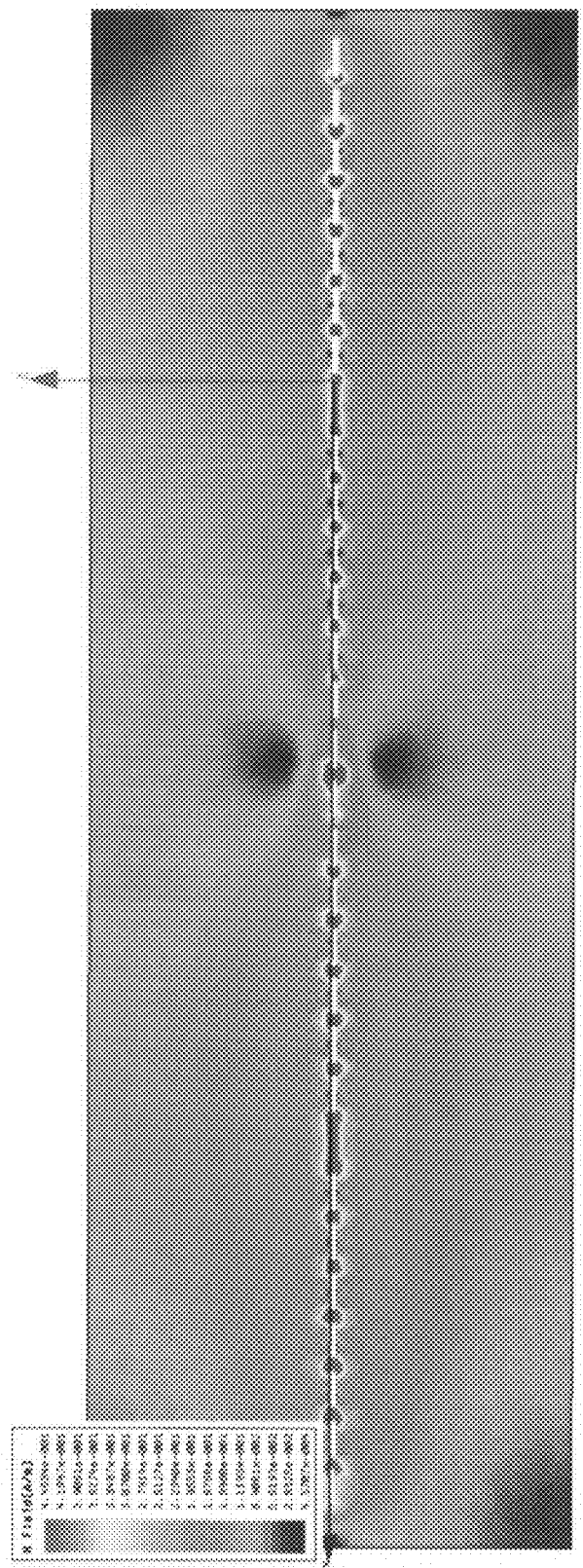
FIG. 30 shows the H field magnitude of two spiral inductors placed side by side.

The sizing of the individual coils is an important aspect of embodiments of the invention. In a specific embodiment, circular inductors are 4.06 em in diameter. The combination of their large size and chosen shape, an array of these inductors generates an uneven magnetic field in a one layer configuration, as shown in FIG. 30, which shows the H field magnitude of two spiral inductors placed side by side. Note the large variance in magnetic field intensity in FIG. 30. An array of square inductors that are 75% smaller than the inductors of FIG. 30 can achieve a more even magnetic field. The magnetic field distribution can then have many small peaks and valleys rather than a few large ones. A receiving unit can enclose these densely packed peaks and valleys simultaneously, resulting in an even distribution of charge.

Figure 33:
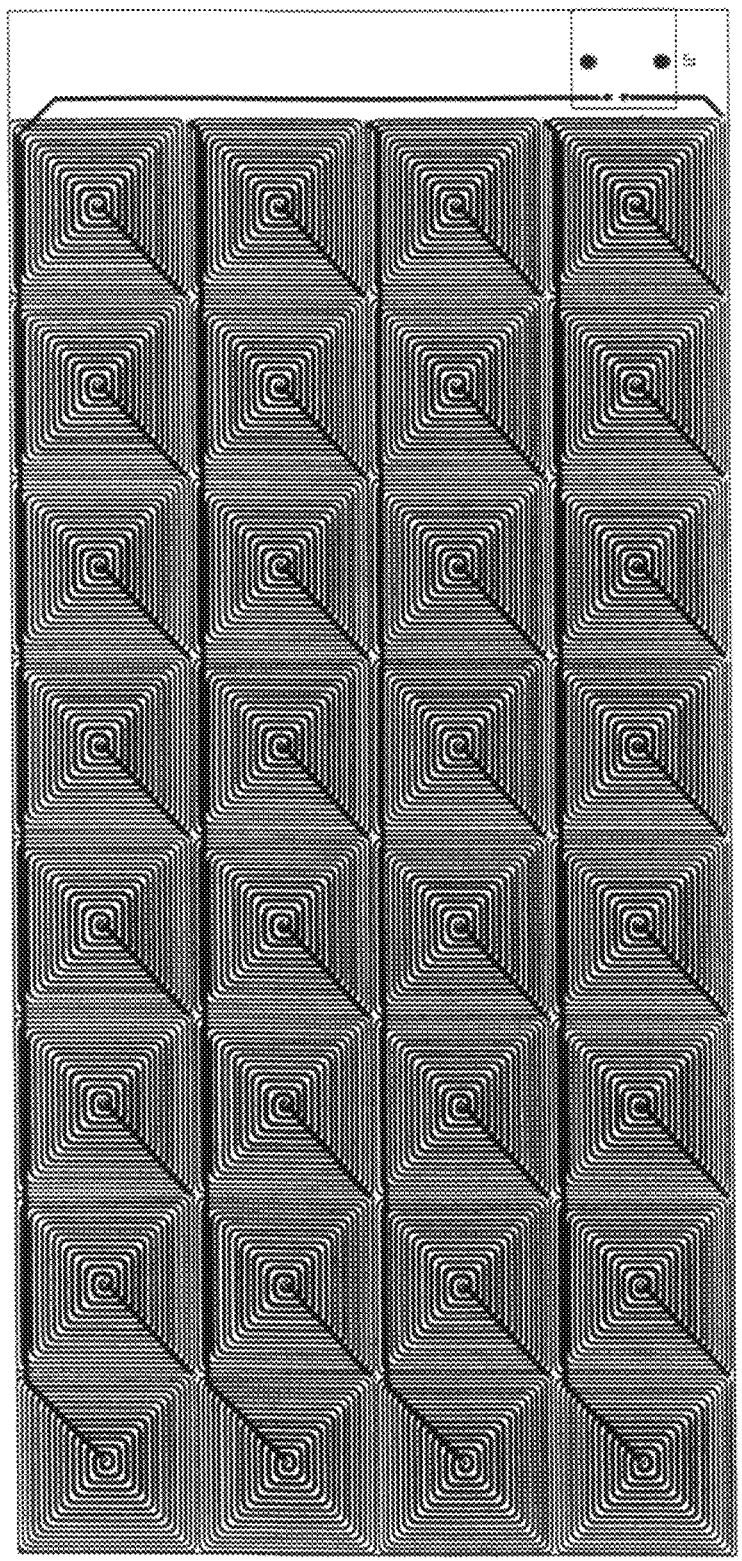
FIG. 33 shows an embodiment of a PowerPad spiral inductor array layout in accordance with the subject invention.

In an embodiment, a PowerPad utilizes a single layer array of inductive coils. A single layer array of inductive coils can reduce, or eliminate, destructive inference patterns that can be associated with a multi-layer structure and can reduce efficiency. The system level effects of such destructive interference are evidenced by the concave voltage distribution shown in FIG. 15 and FIG. 21. FIG. 33 shows a specific embodiment of a PowerPad utilizing a single layer of inductive coils 220. The trace width of each spiral inductor or coil increases toward the center of the spiral. In addition, the spirals arc shaped like a square in this embodiment to provide a more even magnetic field distribution. Finally, the corners of the traces have been rounded to reduced current crowding effect.

The voltage gain achieved by operating at resonance can be useful for offsetting the coupling losses associated with coreless operation. In embodiments, coreless operation can nearly match the performance of traditional transformers [4].

Figure 31:
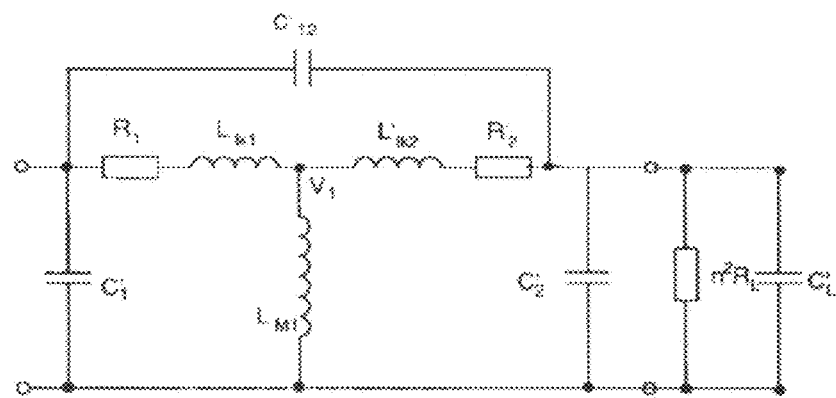
FIG. 31 shows a circuit equivalent of a planar, coreless PCB transformer.

Matching the system to the resonant frequency can be useful. It is also possible to match the resonant frequency to the system by, for example, the addition of a parallel capacitor on the secondary side. Standard transformer models can be applied to PCB transformers to permit tuning of the resonant frequency with relative accuracy. The model schematic and description of the components for a specific embodiment is shown below in FIG. 31 and in Table 5.1, respectively. FIG. 31 shows a circuit equivalent of a planar, coreless PCB transformer.

TABLE 5.1 [5]

Figure 31 circuit component descriptions

| Part Label (Figure 31) | Description |
| --- | --- |
| $R_1$ | Primary winding resistance |
| $R'_2$ | Secondary winding resistance referred to primary |
| $R_L$ | Resistive load |
| $L_{lk1}$ | Primary leakage inductance |
| $L'_{lk2}$ | Secondary leakage inductance referred to primary |
| $L_{M1}$ | Primary mutual inductance |
| $C_1$ | Primary winding capacitance |
| $C'_2$ | Secondary winding capacitance referred to primary, Includes $C'_L$ (Load Capacitance) |
| $C_{12}$ | Capacitance between primary and secondary windings |
| n | Turns Ratio |

Using the above variables and the following equations it is possible to tune the resonant frequency and predict voltage gain. These methods ensure that resonance occurs at a frequency that is within the capabilities of contemporary power electronics.

$$f_0 = \frac{1}{2\pi * \sqrt{L_{eq}C_{eq}}} \quad \text{Resonant Frequency} \quad [5]$$

$$L_{eq} = L'_{lk2} + L_{lk1} \| L_{M1}$$

$$C_{eq} = C'_{eq} + C'_{12}$$

$$\frac{V_2}{V_1} = \frac{\frac{1}{X_1} + sC'_{12}Y_1}{nY} \quad \text{Voltage Gain} \quad [5]$$

$$X_1 = R_1 + sL_{lk1}$$

$$X_2 = R'_2 + sL'_{lk2}$$

$$Y_1 = X_2\left[\frac{1}{X_1} + \frac{1}{sL_{M1}}\right] + 1$$

$$Y_2 = \frac{1}{X_2} + sC'_{12} + sC'_2 + \frac{1}{n^2R_L}$$

$$Y = -\frac{1}{X_2} + Y_1Y_2$$

Figure 32:
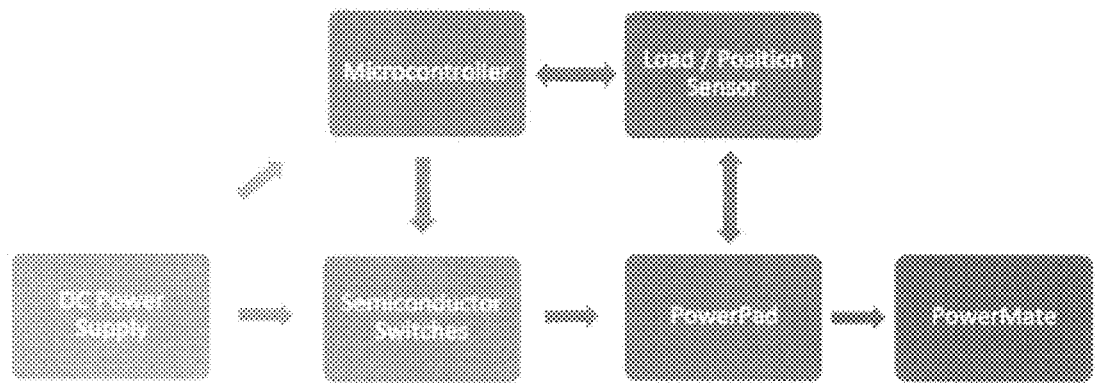
FIG. 32 shows a block diagram of an embodiment of a PowerPad having six components, in accordance with the subject invention.

Referring to FIG. 32, a specific embodiment of the PowerPad system 300 can be broken into six operational components: a DC supply 310, a microcontroller 320, semiconductor switches 330, a PowerPad 340, a sensing mechanism 350, and a PowerMate 360. Referring to FIG. 32, the DC Power Supply can convert wall power to DC outputs that supply a microcontroller and one or more sets of high frequency switches. The microcontroller interfaces with a sensing mechanism to identify the size, position, and load impedance of devices on the PowerPad. The microcontroller uses this information to activate appropriate sections of the PowerPad. Algorithms that anticipate the resonant frequency in relation to size of load, position and orientation permit the microcontroller to adjust the switching frequency in order to maximize the efficiency of power transfer. The semiconductor switches convert DC power into a high frequency AC signal. Gate drivers switch a half bridge inverter, full bridge inverter, or similar circuit design that produces the appropriate signal as efficiently as possible. Each region of the Power Pad can be powered by a separate set of switches. The PowerPad uses independently controlled regions of series connected PCB, spiral inductors to create a substantially even time-varying magnetic field over its surface. Spiral inductors create peak magnetic fields towards their center. To compensate for this phenomenon, the inductors are small and arranged such that traces become increasing wide as they spiral towards the center. The PowerPad uses near-field EM coupling to transfer electric power from the PowerPad to the PowerMate. A sensing mechanism, such as electrical and/or optical sensors, monitor the surface of the PowerPad and interface with the microcontroller. This allows the system to conserve power when no devices are present and also allows the microcontroller to determine the appropriate active regions and operating frequency. The receiving device, which can be referred to as a PowerMate, includes one or more coils that magnetically couple to the PowerPad. A device equipped with a PowerMate receives charge when it is placed in the PowerPad's time varying magnetic field.

Similar to any far-field antenna system that transmits RF signal or power from one location to a remote location, the efficiency of power transfer degrades due to various losses in the system. These losses include the conductor loss in coils, the dielectric loss in substrates where coils are fabricated, the coupling loss between coils, and the impedance mismatch loss. Additionally, there are conversion losses in the power electronics when converting from 60 Hz AC at the wall, to RF power at PowerPad, and converting from RF power to DC power at the PowerMate. Electromagnetic (EM) Design & Impedance Mismatches, Field Distribution &. Adaptive Networks, Conductor Loss & Parasitic Components, EM Field Concentration, and Power Electronics.

Embodiments of the invention utilize EM optimization, impedance matching, and operation at resonance. The coupling loss between coils and the impedance mismatch loss are the two major losses affecting efficiency. In near-field, these two are coupled together and can be characterized by measuring the resonance. Maximum voltage gain and efficiency occur when the system operates at its resonant frequency. At resonance, there is a strong coupling between coils and the PowerPad "sees" the load resistance from the PowerMate through coupling. In this case, the impedance can be matched and there is no mismatch loss. The stronger the coupling, the more the PowerPad will see the load resistance of PowerMate and the coupling loss will be reduced. When the coils are not coupled well, the PowerPad cannot "see" the load resistance from PowerMate, which results in a significant impedance mismatch loss. The frequency response of the impedance measurement will show a loss of resonance. To improve the efficiency, the coupling between coils can be enhanced by using EM design optimization and by creating an impedance matching network that has a large tolerance for impedance mismatches.

Additionally, stand-alone planar coils resonate at frequencies outside of the range of contemporary power electronics. At high frequencies switching losses can be unacceptably large. The resonant frequency is controllable depending on coil design and secondary side capacitance. Computer simulations can be performed to identify the resonant frequency and assist in optimizing the resonant frequency.

Customization of the field distribution and the use of adaptive networks can be used to improve the coupling coefficient. The coupling coefficient depends on the relative positions of the coils and the load impedance. Additionally, powering multiple receivers simultaneously can also alter the resonant frequency. Therefore, when one or more PowerMate receivers are placed arbitrarily on the PowerPad, the efficiency can be improved by customizing the magnetic field distribution and using adaptive networks. In order to adjust to the resonant frequency, the system can use feedback from sensors, such as electrical, optical, pressure or sensors, to detect the impedance mismatch and allow the use of adaptive impedance matching networks to tune the resonance. A sensing mechanism can be incorporated on the PowerPad to detect the impedance mismatch that shifts the resonant frequency and can include an adaptive impedance matching network to tune the resonance.

Power is lost in the driving circuit and the base station due to resistive components and unbalanced impedance. The conductor loss in coils can be minimized by increasing the metal thickness and line width. At frequencies below 10 MHz, the skin depth is larger than 25 urn. To reduce the conductor loss due to skin depth effect, the metal thickness should be more than twice of the skin depth. The standard metal thickness of FR4 PCB is 1.4 mils (35 urn). Therefore, substrates with a thicker metal layer can be used, or additional metal can be plated to increase the thickness. For the metal line width, it can only be increased up to a certain limit due to the finite size of the PowerPad and the requirement of uniform field distribution. The line width can be optimized with the layout of coils. Non-uniform line widths can be used to reduce the conductor loss and its effect on field distribution.

Power is wasted when the entire PowerPad is active and only a small device is placed on its surface. To reduce these losses, the PowerPad coil array can be divided into several sections with integrated sensors that detect the presence of Power Mate coils. This approach deactivates unnecessary PowerPad coils and concentrates the EM field near the PowerMate to improve the overall efficiency. A controller can be utilized to enable power transfer when a device is placed on the boundary of two or more regions.

Reduction of losses in power electronics can allow the system to operate at higher, potentially more efficient frequencies. Contemporary power electronics demonstrate significant switching losses beyond a few megahertz. An efficient power supply that operates at the frequencies required by the PowerPad system can be utilized.

All patents, patent applications, provisional applications, and publications referred to or cited herein are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application.

REFERENCES

[1] S. Y. R. Hui, Wing. W. C. Ho, "A New Generation of Universal Contactless Battery Charging Platform for Portable Consumer Electronic Equipment," IEEE Power Electronics, May 2005.

[2] S. C. Tang, S. Y. Hui, "Evaluation of the Shielding Effects on Printed Circuit Board Transformers using Ferrite Plates and Copper Sheets," IEEE. Power Electronics, November 2002.

[3] S. C. Tang, S. Y. Hui, Shu-Hung Chung, "Characterization of Coreless Printed Circuit Board Transformers," IEEE Power Electronics, November 2000.

[4] S. C. Tang, S. Y. Hui, Shu-Hung Chung, "A Low Profile Power Converter Using PCB Power Transformer with Ferrite Polymer Composite," IEEE Power Electronics, July 2001.

[5] S. C. Tang, S. Y. Hui, Shu-Hung Chung, "Optimal Operation of Coreless PCB Transformer Sate Drive Circuits with Wide Switching Frequency Range," IEEE Power Electronics, May 1999.

[6] Fairchild Semiconductor, "Induction Heating System Topology Review," July 2000.

[7] Huan-Shang Tsai, Jenshan Lin, Robert C. Frye, King L. Tai, Maureen Y. Lau, Dean Kossives, Frank Hrycenko, Young-Kai Chen, Bell Laboratories, "Investigation of Current Crowding Effect of Spiral Inductors," IEEE, 1997.

[8] Don Hui, Shu Yisheng, Zhao Baishan, Dalian Maritime University, "Research on the Electromagnetic Radiation of A PCB Planar Inductor," IEEE, 2005.

[9] Jenshan Lin, "Antenna Systems-Notes on FCC Rules and RF Safety," 2006.

[10] Faye Li, Demetri Giannopouls, lhor Wacyk, Philips Research, "A Low Loss HighFrequency Half Bridge Driver with Integrated Power Devices using EZ-HV SOI Technology," IEEE, 2002.

[11] M. Peter, H. Hein, F. Oehler, P. Baureis, "Planar Inductors with Subdivided Conductors for Reducing Eddy Current Effects," IEEE. 2003.

[12] Splashpower Inc., Patent Application 0210106, November, 2003.

[13] Splashpower Inc., "Frequently Asked Questions" Feb. 20, 2005. Online: www.splashpower.com.

[14] The Wall Street Journal, "Stocks Research", Feb. 20, 2005. Online: www.wsj.com.

[15] HotSpotzz Network, "WiFi Market Information and Statistics," February, 2003. Online: http://www.hotspotzz.com/resource/WiFi stats.pdf.

[16] Express PCB, "Manufacturing Specs," February 2006. Online: http://www.expresspcb.com/ExpressPCBHtm/Specs.htm.
[17] WiFi Net News, "Laptop Sales Pass Desktop Sales," February 2006 Online: http://wifinetnews.com/archives/006258.html.
[18] Network. World, "Juniper, Foundry size up Router Race," June 2000. Online: http://www.networkworld.com/archive/2000/98086 06-05-2000.html.
[19] CBS News, "Microsoft Debuts Wireless Mouse," September 2003. Online: http://www.cbsnews.com/stories/2003/09122/tech/main574453.shtml.
[20] Bluetooth, "Bluetooth History," February 2006. Online: http://www.bluetooth.com/Bluetooth/SIG/Who/History/.
[21] Bluetooth Technology, "History of Bluetooth," July 2005. Online: http://www.du.edu/---ccfergus/bluetooth-web/history.htm.
[22] Farber, Dan, "Highlight Reel from the D conference," ZDNet, June 2006. Online: http://blogs.zdnet.com/BTL1?p=3132
[23] Ryan Tseng, Henoch Senbetta, Roopak Shah, "Business Plan-PowerPad Company," April, 2006.

The invention claimed is:

1. A coil configured to generate a wireless field, the coil comprising: a planar spiral inductor the planar spiral inductor located in a plane and having a conductive trace having an increasing width which does not decrease from an outer periphery of the planar spiral inductor to the center of a spiral formed by the planar spiral inductor.

2. The coil according to claim 1, further comprising: at least one additional planar spiral inductor, wherein the width of each of the at least one additional planar spiral inductor's trace becomes wider as the trace spirals toward the center of a spiral formed by the at least one additional planar spiral inductor, and wherein the widening of each trace as the trace spirals toward the center of the spiral formed by the at least one additional planar spiral inductor produces a more even magnetic field distribution.

3. The coil according to claim 2, wherein the planar spiral inductor and the at least one additional planar spiral inductor form an array of planar spiral inductors, the array of planar spiral inductors being positioned parallel to a surface, and wherein the array of planar spiral inductors is configured to produce a wireless field extending beyond the surface.

4. The coil according to claim 1, wherein the planar spiral inductor has a square shape.

5. The coil according to claim 1, wherein the trace becomes thicker as the trace spirals toward the center of the spiral formed by the planar spiral inductor.

6. The coil according to claim 4, wherein the square shaped planar spiral inductor has smoothed corners configured to reduce a current crowding effect.

7. The coil of claim 1, wherein the coil comprises an RF coil.

8. A system for providing power to a device, the system comprising:
a base station, the base station comprising a planar spiral inductor forming a spiral, the planar spiral inductor located in a plane and having a conductive trace having an increasing width which does not decrease from an outer periphery of the planar spiral inductor to the center of the spiral formed by the planar spiral inductor;
a power supply configured to drive the planar spiral inductor to generate a wireless field having a charging region; and
a device including a receiver, the receiver configured to receive power via the wireless field when the receiver is positioned within the charging region of the planar spiral inductor and to provide power to the device based on the received power.

9. The system according to claim 8, wherein the base station further comprises: at least one additional planar spiral inductor, wherein the width of each of the at least one additional planar spiral inductor's trace becomes wider as the trace spirals toward the center of a spiral formed by the at least one additional planar spiral inductor, and wherein the widening of each trace as the trace spirals toward the center of the spiral formed by the at least one additional planar spiral inductor produces a more even magnetic field distribution.

10. The system according to claim 9, wherein the planar spiral inductor and the at least one additional planar spiral inductor form an array of planar spiral inductors, wherein the array of planar spiral inductors are positioned parallel to a surface.

11. The system according to claim 10, wherein the array of planar spiral inductors are separated into two or more separate regions, and wherein each separate region is configured to be activated only when a receiver is located in the charging region of the separate region.

12. The system according to claim 10, further comprising: a sensing mechanism configured to identify a load impedance of devices located in the charging region of the array of planar spiral inductors; and a microcontroller configured to adjust the power supply to increase the efficiency of power transfer from the array of planar spiral inductors to the devices located in the charging region of the array of planar spiral inductors.

13. The system according to claim 10, further comprising: a plurality of sensors, wherein the plurality of sensors are configured to detect the impedance mismatch between the array of planar spiral inductors and devices located in the charging region of the array of planar spiral inductors; and an adaptive impedance matching network, wherein the adaptive impedance matching network tunes the array of planar spiral inductors to resonate based on the impedance mismatch detected by the sensors.

14. The system according to claim 10, wherein the thickness of each planar spiral inductor of the array of planar spiral inductors is greater than two times the skin depth of the planar spiral inductor.

15. A method of providing power to a device including a receiver, the method comprising:
generating a wireless field, the wireless field having a charging region, the wireless field generated via a planar spiral inductor forming a spiral, the planar spiral inductor located in a plane and having a conductive trace having an increasing width which does not decrease from an outer periphery of the planar spiral inductor to the center of the spiral formed by the planar spiral inductor;
transmitting power via the wireless field to a receiver located within the charging region, the receiver configured to provide power to the device.

16. The method according to claim 15, wherein the wireless field is generated via at least one additional planar spiral inductor, wherein the width of each of the at least one additional planar spiral inductor's trace becomes wider as the trace spirals toward the center of a spiral formed by the at least one additional planar spiral inductor, and wherein the widening of each trace as the trace spirals toward the center of the spiral formed by the at least one additional planar spiral inductor produces a more even magnetic field distribution.

17. The method according to claim 16, wherein the planar spiral inductor and the at least one additional planar spiral inductor form an array of planar spiral inductors, wherein the array of planar spiral inductors are positioned parallel to a surface.

18. The method according to claim 17, wherein the array of planar spiral inductors are separated into two or more separate regions, and wherein each separate region is configured to be activated only when a receiver is located in the charging region of the separate region.

19. The method according to claim 17, further comprising: identifying a load impedance of devices located in the charging region of the array of planar spiral inductors; and adjusting the power supply to increase the efficiency of power transfer from the array of planar spiral inductors to the devices located in the charging region of the array of planar spiral inductors.

20. The method according to claim 17, further comprising detecting the impedance mismatch between the array of planar spiral inductors and devices located in the charging region of the array of planar spiral inductors; and providing an adaptive impedance matching network, wherein the adaptive impedance matching network tunes the array of planar spiral inductors to resonance based on the detected impedance mismatch.

21. The method according to claim 17, wherein the thickness of each planar spiral inductor of the array of planar spiral inductors is greater than two times the skin depth of the corresponding planar spiral inductor.

22. A system, comprising:
means for generating a wireless field having a charging region for powering a device, the means for generating the wireless field comprising a planar spiral inductor, the planar spiral inductor located in a plane and having a conductive trace having an increasing width which does not decrease from an outer periphery of the planar spiral inductor to the center of a spiral formed by the planar spiral inductor; and
means for supporting a receiver, the receiver configured to receive power from the planar spiral inductor when the receiver is positioned within the charging region so as to provide power to the device.

23. The system according to claim 22, further comprising at least one additional planar spiral inductor, wherein the width of each of the at least one additional planar spiral inductor's trace becomes wider as the trace spirals toward the center of a spiral formed by the at least one additional planar spiral inductor, and wherein the widening of each trace as the trace spirals toward the center of the spiral formed by the at least one additional planar spiral inductor produces a more even magnetic field distribution.

24. The system according to claim 23, wherein the planar spiral inductor and the at least one additional planar spiral inductor form an array of planar spiral inductors, wherein the array of planar spiral inductors are positioned parallel to a surface.

* * * * *